United States Patent
Hudlický et al.

(10) Patent No.: US 10,196,337 B2
(45) Date of Patent: Feb. 5, 2019

(54) PROCESSES FOR THE PREPARATION OF HYDROXYLATED CYCLOHEXYL COMPOUNDS

(71) Applicants: Tomáš Hudlický, St. Catherines (CA); Jordan Thomas Froese, Fonthill (CA)

(72) Inventors: Tomáš Hudlický, St. Catherines (CA); Jordan Thomas Froese, Fonthill (CA)

(*) Notice: Subject to any disclaimer, the term of this patent is extended or adjusted under 35 U.S.C. 154(b) by 0 days.

(21) Appl. No.: 15/450,223

(22) Filed: Mar. 6, 2017

(65) Prior Publication Data
US 2017/0253550 A1    Sep. 7, 2017

Related U.S. Application Data

(60) Provisional application No. 62/303,444, filed on Mar. 4, 2016.

(51) Int. Cl.
C07C 45/59    (2006.01)
C07C 49/743    (2006.01)

(52) U.S. Cl.
CPC ............ *C07C 45/59* (2013.01); *C07C 49/743* (2013.01)

(58) Field of Classification Search
CPC .................................................... C07C 45/59
USPC ........................................................ 568/343
See application file for complete search history.

(56) References Cited

PUBLICATIONS

Eaton et al. J. Nat. Prod. 2015, 78, 1752-1755.*
Froese, J. et al., "Chemoenzymatic Synthesis of Pleiogenone A: An Antiproliferative Trihydroxyalkylcyclohexenone Isolated from Pleiogynium", Chem. Eur. J. 2016, 22, 6180-6184.
Eaton, A.L., et al., "Antiproliferative Trihydroxyalkylcyclohexenones from Pleiogynium Timoriense", Journal of Natural Products, 2015, 78, 1752-1755.
Eaton, A.L. et al., "Correction to Antiproliferative Trihydroxyalkylcyclohexenones from Pleiogynium timoriense", J. Nat. Prod. 2016, 79:2, 451, DOI: 10.1021/acs.jnatprod.6b00073.
Reiner, A.M. et al., "Metabolism of benzoic acid by bacteria. Accumulation of (-),5-cyclohexadiene-1,2-diol-1-carboxylic acid by a mutant strain of Alcaligenes eutrophus" Biochemistry 1971, 10, 2530-2536.
Lewis, S.E., "Applications of biocatalytic arene ipso,ortho cis-dihydroxylation in synthesis" Chem. Commun. 2014, 50, 2821-2830.
Adams, D.R., "The Use of Ipso-dihydrodiols Enzymatically Derived from Benzoic Acid in Enantioselective Synthesis. Appoaches to Total Synthesis of Vinca Alkaloids", 2014, Ph.D. Thesis, Brock University.
Adams, D.R. et al., "Chemoenzymatic Approach to Synthesis of Hydroxylated Pyrrolidines from Benzoic Acid", Heterocycles, 2014, 88:2, 1255-1274.
Ghavre, M. et al., "A formal Approach to Xylosmin and Flacourtosides E and F: Chemoenzymatic Total Synthesis of the Hydroxylated Cyclohexenone Carboxylic Acid Moiety of Xylosmin.", Organic Letters. 2017, 19:1156-1159.
Hudlicky, T. et al., "Enzymatic Dihydroxylation of Aromatics in Enantioselective Synthesis: Expanding Asymmetric Methodology", Aldrichimica Acta, 1999, 32:2, 33-72.
Banwell, M. G., "Chemoenzymatic Methods for the Enantioselective Preparation of Sesquiterpenoid Natural Products from Aromatic Precursors", Pure and Applied Chemistry, 2003, 75:2-3. 223-229.
Johnson, R. A., "Microbial Arene Oxidations", Organic Reactions, 2004, 63, 117-159.
Rinner, U., Chiral Pool Synthesis: Chiral Pool Syntheses from cis-Cyclohexadiene Diols, Elsevier Ltd., 2012, 240-267.
Hudlicky, T. et al., "Celebrating 20 Years of SYNLETT—Special Account on the Merits of Biocatalysis and the Impact of Arene cis-Dihydrodiols on Enantioselective Synthesis", Department of Chemistry and Centre for Biotechnology, Brock University, 2008, 685-704.
Hudlicky, T. et al., "Applications of Biotransformations and Biocatalysis to Complexity Generation in Organic Synthesis", Chem. Soc. Rev., 2009, 38, 3117-3132.
Banwell, M. G. et al., "Chemoenzymatic Pathways for the Synthesis of Biologically Active Natural Products", Journal & Proceedings of the Royal Society of New South Wales, 2016, 149:1-2, 34-50.
Griffen, Julia A. et al., "Benzoate Dioxygenase from Ralstonia Eutropha B9-Unusual Regiochemistry of Dihydroxylation Permits Rapid Access to Novel Chirons", Organic Chemistry Frontiers, 2004, 1, 79,-90.
Lewis, S.E. in "Arene Chemistry: Reaction Mechanisms and Methods for Aromatic Compounds", Mortier, J., Ed., Wiley-VCH, 2015; p. 915-937.

* cited by examiner

*Primary Examiner* — Ana Z Muresan
(74) *Attorney, Agent, or Firm* — Bereskin & Parr LLP/S.E.N.C.R.L., S.R.L.; Patricia Folkins

(57) ABSTRACT

The present application relates to processes for the preparation of polyhydroxylated cyclohexyl compounds of Formula I:

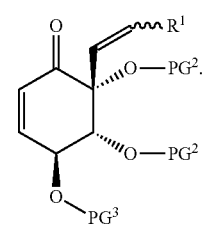

20 Claims, No Drawings

PROCESSES FOR THE PREPARATION OF HYDROXYLATED CYCLOHEXYL COMPOUNDS

CROSS-REFERENCE TO RELATED APPLICATIONS

The present application claims the benefit of priority from co-pending U.S. provisional application No. 62/303,444 filed on Mar. 4, 2016, the contents of which are incorporated herein by reference in their entirety.

FIELD

The present application relates to processes for the preparation of hydroxylated 6-membered carbocyclic compounds, in particular polyhydroxylated cyclohexenones.

BACKGROUND

Several hydroxylated cyclohexenones recently reported have been shown to have potent biological activities. Alkylcyclohexenones 1, 2 and 3, Scheme 1 (named pleiogenones A, B and C, respectively), were isolated from the extract of the bark of *Pleiogynium timorense* and displayed $IC_{50}$ values of 0.8, 0.7, and 0.8 μM, respectively, against the A2780 ovarian cancer cell line[1] but their synthesis has not previously been reported.

Scheme 1

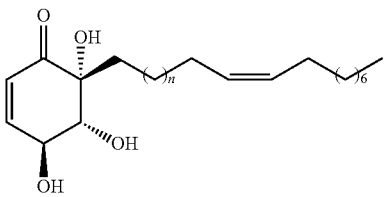

1 n = 5
2 n = 7
3 n = 9

SUMMARY

A process for the first enantioselective synthesis of 1 from benzoic acid is disclosed herein. The process is versatile and readily amenable to the preparation of a variety of analogs of 1 as well as other polyhydroxylated cyclohexyl compounds.

Accordingly, the present application includes a process for the preparation of a compound of Formula I:

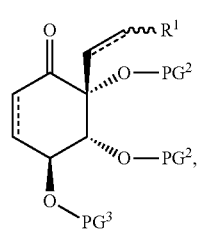

I wherein
both ----- represent either a single bond or a double bond;

the process comprising:

(a) protecting a compound of Formula II under conditions to provide a compound of Formula III:

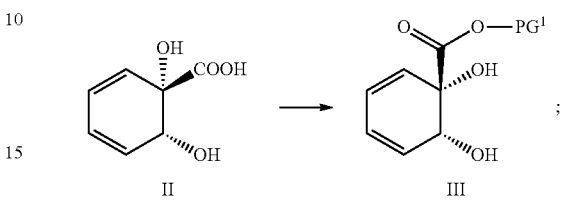

II  III (b) protecting the compound of Formula III under conditions to provide a compound of Formula IV:

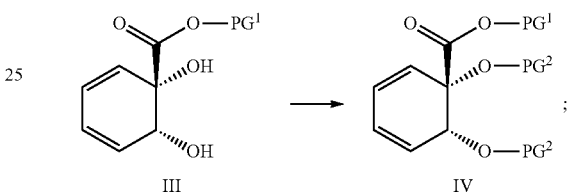

III  IV (c) reacting the compound of Formula IV with a first reducing agent under conditions to provide a compound of Formula V:

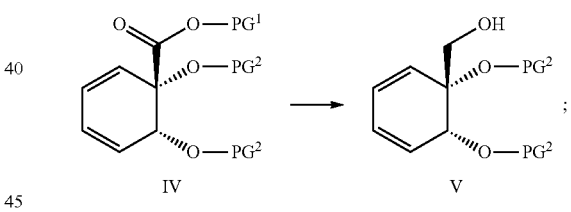

IV  V (d) reacting the compound of Formula V with a first oxidizing agent under conditions to provide a compound of Formula VI:

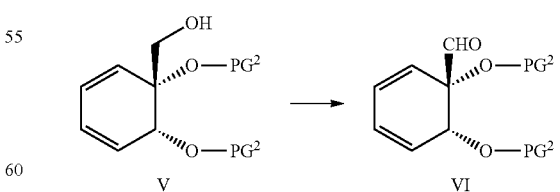

V  VI (e) reacting the compound of Formula VI with an alkene-forming reagent of Formula VII under conditions to provide a compound of Formula VIII:

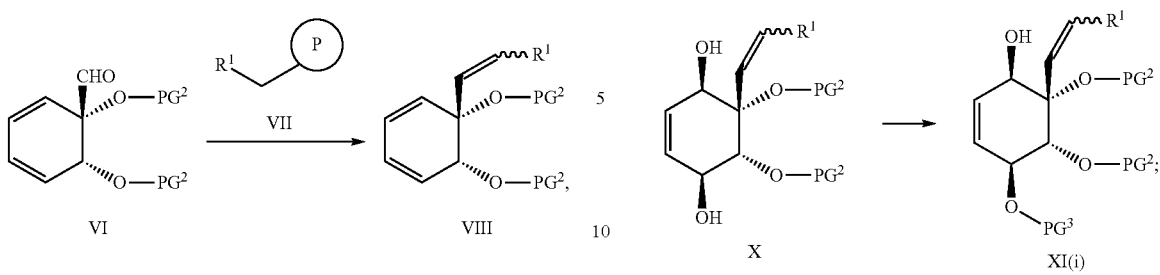

wherein the alkene-forming reagent is a Wittig reagent and

P represents a triphenylphosphonium moiety or the alkene-forming reagent is a Horner-Wadsworth-Emmons reagent and

P represents a phosphonate moiety;

(f) reacting the compound of Formula VIII with a source of singlet oxygen under conditions to provide an endoperoxide of formula IX:

(g) reacting the endoperoxide of Formula IX with a second reducing agent under conditions to provide a compound of Formula X:

(h-I) when both ══ in the compound of Formula I are a double bond, protecting the compound of Formula X under conditions to provide a compound of Formula XI(i):

and (i-I) reacting the compound of Formula XI(i) with a second oxidizing agent under conditions to provide the compound of Formula I, or (h-II) when both ══ in the compound of Formula I are a single bond, hydrogenating the compound of Formula X under conditions to provide a compound of Formula XIX and protecting the compound of Formula XIX under conditions to provide a compound of Formula XI(ii):

and (i-II) reacting the compound of Formula XI(ii) with a second oxidizing agent under conditions to provide the compound of Formula I;

wherein $PG^1$, $PG^2$ and $PG^3$ are each independently protecting groups, wherein $PG^1$ is a protecting group that is removed by the first reducing agent and each $PG^2$ is the same or different or both $PG^2$ are joined to form a cyclic protecting group;

$R^1$ is a functional group that is converted into the functional group of a known natural product or a functional analog thereof; and wherein in the compounds of Formulae I, VII, VIII, IX, X, XI(i), XI(ii) and XIX, one or more available hydrogens in $R^1$ is/are optionally replaced with F and/or one or more of available atoms in $R^1$ is/are optionally replaced with an isotopic label.

The present application also includes also includes a process for the preparation of a compound of Formula XII:

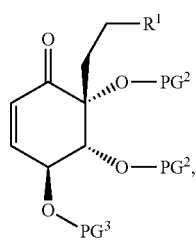

XII the process comprising:
(a) protecting a compound of Formula I(i) under conditions to provide a compound of Formula XIII:

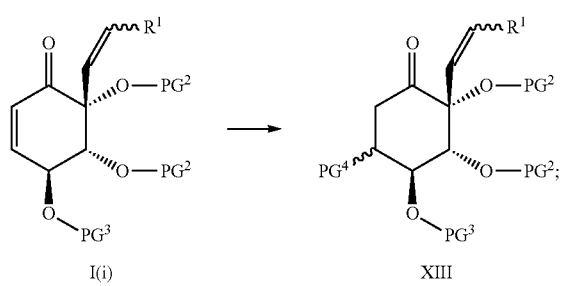

(b) hydrogenating the compound of Formula XIII under conditions to provide a compound of Formula XIV:

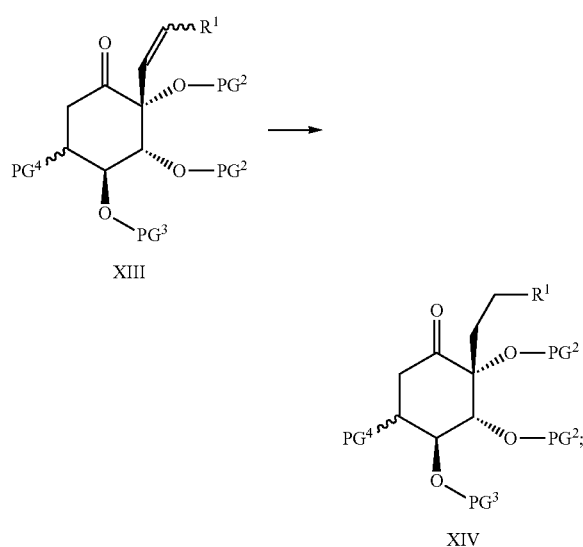

and
(c) deprotecting the compound of Formula XIV under conditions to remove $PG^4$ and provide the compound of Formula XII,
wherein
  $PG^2$ and $PG^3$ are each independently protecting groups
  $R^1$ is a functional group that is converted into the functional group of a known natural product or a functional analog thereof;
  $PG^4$ is a protecting group; and
wherein in the compounds of Formulae I(i), XII, XIII and XIV, one or more available hydrogens in $R^1$ is/are optionally replaced with F and/or one or more of available atoms in $R^1$ is/are optionally replaced with an isotopic label.

In an embodiment, the compound of Formula XII is a compound of Formula XII(a):

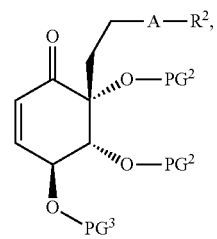

XII(a)

wherein
  $PG^2$ and $PG^3$ are each independently protecting groups;
  A is $C_{1-20}$alkylene;
  $R^2$ is a functional group that is converted into an aldehyde; and
wherein in the compound of Formula XII(a), one or more available hydrogens in A and $R^2$ is/are optionally replaced with F and/or one or more of available atoms in A and $R^2$ is/are optionally replaced with an isotopic label.

Accordingly, the present application also includes a process for the preparation of a compound of Formula XV(i):

XV(i)

wherein
  A is $C_{1-20}$alkylene;
  $R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups; and
  $R^5$, $R^6$ and $R^7$ are each independently H, $C_{1-6}$alkyl or aryl, the process comprising:
(a) reacting a compound of Formula XII(a) under conditions to convert $R^2$ into an aldehyde to provide a compound of Formula XVI(i):

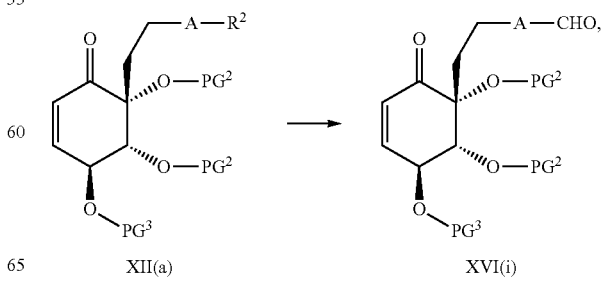

wherein
A is $C_{1-20}$alkylene;
$R^2$ is a functional group that is converted into an aldehyde;
$PG^2$ and $PG^3$ are each independently protecting groups; and
(b) reacting the compound of Formula XVI(i) with an alkene-forming reagent of Formula XVII under conditions to provide a compound of Formula XVII(i):

XVI(i)

XVIII(i)

wherein
the alkene-forming reagent is a Wittig reagent and

Ⓟ represents a triphenylphosphonium moiety or the alkene-forming reagent is a Horner-Wadsworth-Emmons reagent and

Ⓟ represents a phosphonate moiety;
A is $C_{1-20}$alkylene,
$PG^2$ and $PG^3$ are each independently protecting groups; and
$R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups;
(c) deprotecting the compound of Formula XVIII(i) under conditions to provide the compound of Formula XV(i) wherein $R^5$, $R^6$ and $R^7$ are all H; and
(d) optionally reacting the compound of Formula XV(i) wherein $R^5$, $R^6$ and $R^7$ are all H under conditions to convert one or more of $R^5$, $R^6$ and $R^7$ to $C_{1-6}$alkyl or aryl,
wherein in the compounds of Formulae XII(a), XV(i), XVI(i), XVII and XVII(i), one or more available hydrogens in A, $R^2$ and/or $R^3$ is/are optionally replaced with F and/or one or more of available atoms in A, $R^2$ and/or $R^3$ is/are optionally replaced with an isotopic label.

The present application also includes a process for the preparation of a compound of Formula XV(ii):

XV(ii)

wherein
A is $C_{1-20}$alkylene;
$R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups; and
$R^5$, $R^6$ and $R^7$ are each independently H, $C_{1-6}$alkyl or aryl,
the process comprising:
(a) reacting a compound of Formula I(ii) under conditions to convert $R^2$ into an aldehyde to provide a compound of Formula XVI(ii):

I(ii)    XVI(ii)

wherein
A is $C_{1-20}$alkylene;
$R^2$ is a functional group that is converted into an aldehyde;
$PG^2$ and $PG^3$ are each independently protecting groups; and
(b) reacting the compound of Formula XVI(ii) with an alkene-forming reagent of Formula XVII under conditions to provide a compound of Formula XVIII(ii):

XVI(ii)

-continued

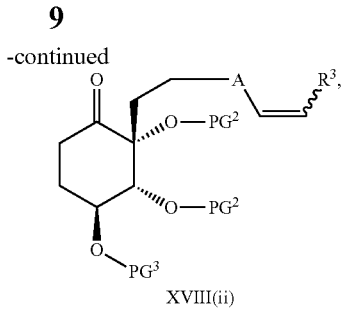

XVIII(ii)

wherein
the alkene-forming reagent is a Wittig reagent and

represents a triphenylphosphonium moiety or the alkene-forming reagent is a Horner-Wadsworth-Emmons reagent and

represents a phosphonate moiety;

A is $C_{1-20}$alkylene;

$PG^2$ and $PG^3$ are each independently protecting groups; and $R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups;

(c) deprotecting the compound of Formula XVIII(ii) under conditions to provide the compound of Formula XV(ii) wherein $R^5$, $R^6$ and $R^7$ are all H; and (d) optionally reacting the compound of Formula XV(ii) wherein $R^5$, $R^6$ and $R^7$ are all H under conditions to convert one or more of $R^5$, $R^6$ and $R^7$ to $C_{1-6}$alkyl or aryl, wherein in the compounds of Formulae I(ii), XV(ii), XVI(ii), XVII and XVIII(ii), one or more available hydrogens in A, $R^2$ and/or $R^3$ is/are optionally replaced with F and/or one or more of available atoms in A, $R^2$ and/or $R^3$ is/are optionally replaced with an isotopic label.

The present application also includes a process for the preparation of a compound of Formula XV(i) or XV(ii):

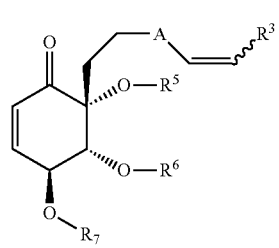

XV(i)

or

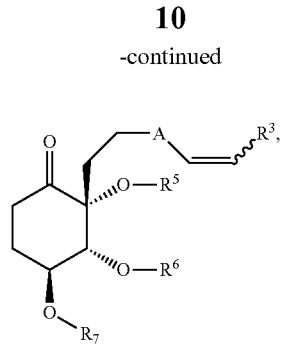

XV(ii)

wherein
A is $C_{1-20}$alkylene;

$R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups; and $R^5$, $R^6$ and $R^7$ are each independently H, $C_{1-6}$alkyl or aryl, the process comprising:

(a) protecting a compound of Formula I(a)(i) under conditions to provide a compound of Formula XIII(a):

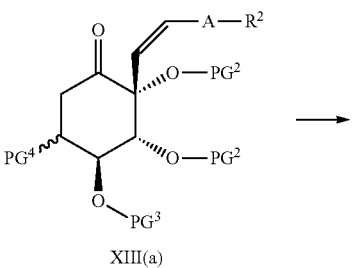

I(a)(i)     XIII(a)

wherein
$PG^2$ and $PG^3$ are each independently protecting groups;
$PG^4$ is a protecting group;
A is $C_{1-20}$alkylene; and
$R^2$ is a functional group that is converted into an aldehyde;

(b) hydrogenating the compound of Formula XIII(a) under conditions to provide a compound of Formula XIV(a):

XIII(a)

-continued

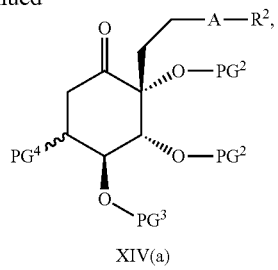
XIV(a)

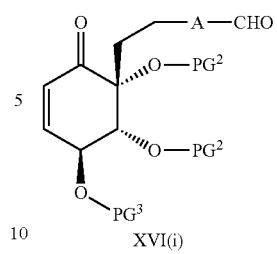
XVI(i)

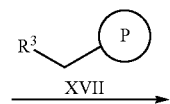
XVII

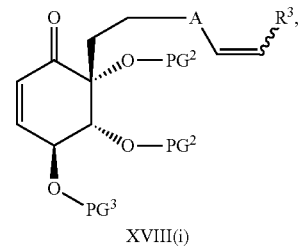
XVIII(i)

wherein
PG² and PG³ are independently protecting groups;
PG⁴ is a protecting group;
A is $C_{1-20}$alkylene; and
R² is a functional group that is converted into an aldehyde;
(c) deprotecting the compound of Formula XIV(a) under conditions to remove PG⁴ and provide a compound of Formula XII(a):

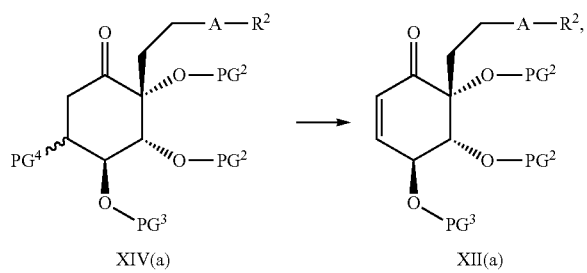

XIV(a) → XII(a)

wherein
PG² and PG³ are each independently protecting groups;
A is $C_{1-20}$alkylene; and
R² is a functional group that is converted into an aldehyde;
(d) reacting the compound of Formula XII(a) under conditions to convert R² into an aldehyde to provide a compound of Formula XVI(i):

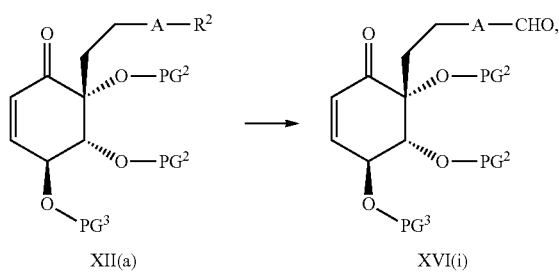

XII(a) → XVI(i)

wherein
PG² and PG³ are each independently protecting groups;
A is $C_{1-20}$alkylene; and
R² is a functional group that is converted into an aldehyde;
(e) reacting the compound of Formula XVI(i) with an alkene-forming reagent of Formula XVII under conditions to provide a compound of Formula XVII(i):

wherein
the alkene-forming reagent is a Wittig reagent and

represents a triphenylphosphonium moiety or the alkene-forming reagent is a Horner-Wadsworth-Emmons reagent and

represents a phosphonate moiety;
PG² and PG³ are each independently protecting groups;
A is $C_{1-20}$alkylene; and
R³ is $C_{1-20}$alkyl, $C_{2-20}$alkenyl, $C_{2-20}$alkynyl, $C_{1-20}$alkylene-R⁴, $C_{2-20}$alkenylene-R⁴ or $C_{2-20}$alkynylene-R⁴, wherein R⁴ is $C_{3-10}$cycloalkyl, aryl or heteroaryl and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups;
(f) deprotecting the compound of Formula XVIII(i) under conditions to provide the compound of Formula XV(i) wherein R⁵, R⁶ and R⁷ are all H;
(g) optionally reacting the compound of Formula XV(i) wherein R⁵, R⁶ and R⁷ are all H under conditions to convert one or more of R⁵, R⁶ and R⁷ to $C_{1-6}$alkyl or aryl; and
(h) either after (f) or (g), optionally hydrogenating the compound of Formula XV(i) under conditions to provide a compound of Formula XV(ii):

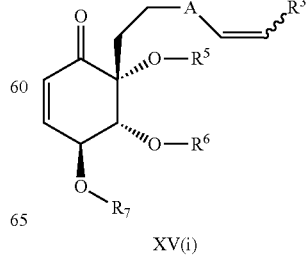
XV(i)

-continued

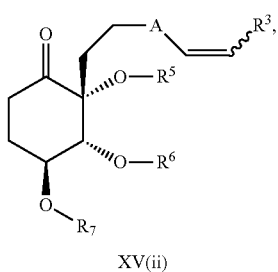

XV(ii)

wherein

A is $C_{1-20}$alkylene;

$R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups; and $R^5$, $R^6$ and $R^7$ are each independently H, $C_{1-6}$alkyl or aryl;

or the process comprising:

(a) reacting a compound of Formula I(a)(ii) under conditions to convert $R^2$ into an aldehyde to provide a compound of Formula XVI(ii):

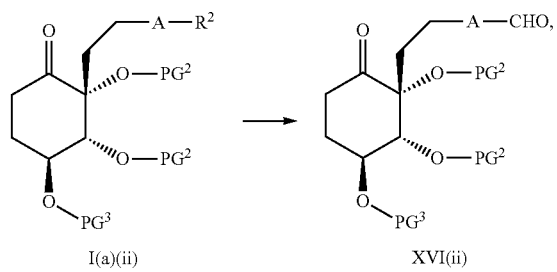

wherein

PG$^2$ and PG$^3$ are each independently protecting groups;

A is $C_{1-20}$alkylene; and $R^2$ is a functional group that is converted into an aldehyde;

(b) reacting the compound of Formula XVI(ii) with an alkene-forming reagent of Formula XVII under conditions to provide a compound of Formula XVIII(ii):

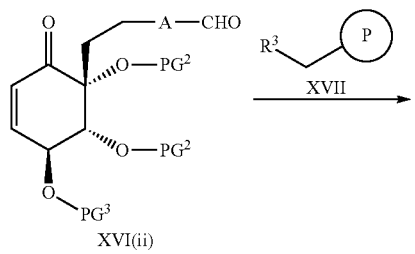

-continued

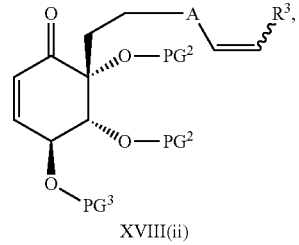

XVIII(ii)

wherein the alkene-forming reagent is a Wittig reagent and

represents a triphenylphosphonium moiety or the alkene-forming reagent is a Horner-Wadsworth-Emmons reagent and

represents a phosphonate moiety;

PG$^2$ and PG$^3$ are each independently protecting groups;

A is $C_{1-20}$alkylene; and $R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups;

(c) deprotecting the compound of Formula XVIII(ii) under conditions to provide the compound of Formula XV(ii) wherein $R^5$, $R^6$ and $R^7$ are all H; and (d) optionally reacting the compound of Formula XV(ii) wherein $R^5$, $R^6$ and $R^7$ are all H under conditions to convert one or more of $R^5$, $R^6$ and $R^7$ to $C_{1-6}$alkyl or aryl, wherein in the compounds of Formulae I(a)(i), I(a)(ii), XII(a), XIII(a), XIV(a), XV(i), XV(ii), XVI(i), XVI(ii), XVII, XVIII(i) and XVIII(ii), one or more available hydrogens in A, $R^2$ and/or $R^3$ is/are optionally replaced with F and/or one or more of available atoms in A, $R^2$ and/or $R^3$ is/are optionally replaced with an isotopic label.

The present application also includes a compound of Formula XV:

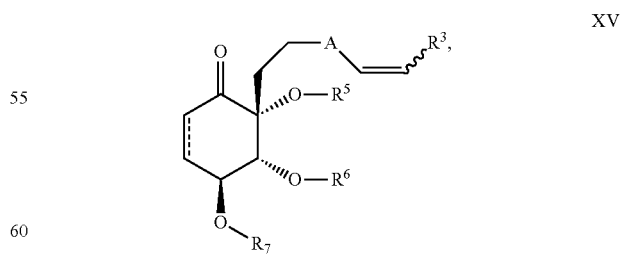

wherein

===== represents either a single bond or a double bond;

$R^3$ is $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl; and $R^5$, $R^6$ and $R^7$ are each independently H, $C_{1-6}$alkyl or aryl; and wherein one or more available hydrogens in $R^3$, $R^5$, $R^6$ and/or $R^7$ is/are optionally replaced with F and/or one or more of available atoms in $R^3$, $R^5$, $R^6$ and/or $R^7$ is/are optionally replaced with an isotopic label.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a reducing agent" should be understood to present certain aspects with one reducing agent or two or more additional reducing agents. In embodiments comprising an "additional" or "second" component, such as an additional or second reducing agent, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "reducing agent" as used herein means any compound or combination of compounds that reduces a desired functional group(s) but does not otherwise react with or degrade the substrate comprising the functional group(s). A reducing agent results in the overall gain of electrons, or in the case of organic chemistry, hydrogen atoms to the functional group.

The term "oxidizing agent" as used herein means any compound or combination of compounds that oxidizes a desired functional group(s) but does not otherwise react with or degrade the substrate comprising the functional group(s). An oxidizing agent results in the overall gain of electrons, or in the case of organic chemistry, a loss of hydrogen atoms from the functional group.

The term "functional analog thereof" in reference to a functional group of a known natural product as used herein means a functional group that is analogous to the functional group of a known natural product with structural variations that do not substantially negate the natural product's desired activity.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions for the reaction to proceed to a sufficient extent to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or process/method steps disclosed herein means that the reactions or process/method steps proceed to an extent that conversion of the starting material or substrate to product is optimized for a given set of conditions. Conversion may be optimized when greater than about 5, 10, 15, 20, 25, 30, 35, 40, 45, 50, 55, 60, 65, 70, 75, 80, 85, 90, 95 or 100% of the starting material or substrate is converted to product.

In embodiments of the present application, the compounds in the processes/methods described herein have at least one asymmetric center. Where compounds possess more than one asymmetric center, they may exist as diastereomers. It is to be understood that all such isomers and mixtures thereof in any proportion are encompassed within the scope of the processes/methods of the present application. It is to be further understood that while the stereochemistry of the compounds in the processes/methods may be as shown in any given compound listed herein, such compounds may also contain certain amounts (e.g. less than 20%, suitably less than 10%, more suitably less than 5%) of compounds having alternate stereochemistry.

In embodiments of the present application, the compounds in the processes/methods described herein have at least one double bond capable of geometric isomerism; for example, the double bond may exist as a cis or a trans isomer. It is to be understood that all such isomers and mixtures thereof in any proportion are encompassed within the scope of the processes/methods of the present application. It is to be further understood that while the isomerism of the compounds in the processes/methods may be as shown in any given compound listed herein, such compounds may also contain certain amounts (e.g. less than 20%, suitably less than 10%, more suitably less than 5%) of the corresponding compound having alternate isomerism.

The term "protecting" as used herein refers to using a chemical moiety, i.e. a "protecting group" of "PG" which protects or masks a reactive portion of a molecule to prevent side reactions in that reactive portion of the molecule, while manipulating or reacting a different portion of the molecule. After the manipulation or reaction is complete, the protecting group is removed under conditions that do not degrade or decompose the remaining portions of the molecule; i.e. the protected reactive portion of the molecule is "deprotected". The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic *Synthesis*", John Wiley & Sons, 3rd Edition, 1999 and in Kocienski, P. Protecting Groups, 3rd Edition, 2003, Georg Thieme Verlag (The Americas). Examples of suitable protecting groups include, but are not limited to t-Boc, $C_{1-6}$acyl, Ac, Ts, Ms, silyl ethers such as TMS, TBDMS, TBDPS, Tf, Ns, Bn, Fmoc, dimethoxytrityl, methoxyethoxymethyl ether, methoxymethyl ether, pivaloyl, p-methyoxybenzyl ether, tetrahydropyranyl, trityl, ethoxyethyl ethers, carbobenzyloxy, benzoyl, methyl, triisopropylsilane triflyl, thiophenyl, cyclic protecting groups such as those comprising —$C(CH_3)_2$— and the like.

The term "polyhydroxylated" as used herein refers to a compound that comprises more than one hydroxyl ("OH") group.

The term "acyl" as used herein, whether it is used alone or as part of another group, means straight or branched chain, saturated acyl groups. The number of carbon atoms that are possible in the referenced acyl group are indicated by the numerical prefix "$C_{n1-n2}$". For example, the term $C_{1-6}$acyl means an acyl group having 1, 2, 3, 4, 5 or 6 carbon atoms.

The term "halo" as used herein refers to a halogen atom and includes F, Cl, Br and I.

t-Boc as used herein refers to the group t-butyloxycarbonyl.

Ac as used herein refers to the group acetyl.

Ts (tosyl) as used herein refers to the group p-toluenesulfonyl.

Ms as used herein refers to the group methanesulfonyl.

TMS as used herein refers to the group trimethylsilyl.

TBDMS as used herein refers to the group t-butyldimethylsilyl.

TBDPS as used herein refers to the group t-butyldiphenylsilyl.

Tf as used herein refers to the group trifluoromethanesulfonyl.

Ns as used herein refers to the group naphthalene sulphonyl.

Bn as used herein refers to the group benzyl.

Fmoc as used herein refers to the group fluorenylmethoxycarbonyl.

The term "solvent" as used herein includes both a single solvent and a mixture comprising two or more solvents.

The term "available", as in "available hydrogen atoms" or "available atoms" refers to atoms that would be known to a person skilled in the art to be capable of replacement by either a fluorine atom (in the case of hydrogen atoms) or isotopic labels (in the case of all atoms) using methods known in the art.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-12}$alkyl means an alkyl group having 1, 2, 3, 4, 5, 6, 7, 8, 9, 10, 11 or 12 carbon atoms.

The term "alkenyl" as used herein, whether it is used alone or as part of another group, means straight or branched chain, unsaturated alkenyl groups. The number of carbon atoms that are possible in the referenced alkenyl group are indicated by the numerical prefix "$C_{n1-n2}$". For example, the term $C_{2-12}$alkenyl means an alkenyl group having 2, 5, 4, 5, 6, 7, 8, 9, 10, 11 or 12 carbon atoms and at least one double bond, for example 1 to 3, 1 to 2 or 1 double bond.

The term "alkynyl" as used herein, whether it is used alone or as part of another group, means straight or branched chain, unsaturated alkynyl groups. The number of carbon atoms that are possible in the referenced alkynyl group are indicated by the numerical prefix "$C_{n1-n2}$". For example, the term $C_{2-12}$alkynyl means an alkynyl group having 2, 5, 4, 5, 6, 7, 8, 9, 10, 11 or 12 carbon atoms and at least one triple bond, for example 1 to 3, 1 to 2 or 1 triple bond.

The term "alkylene" as used herein, whether it is used alone or as part of another group, means straight or branched chain, saturated alkylene group, that is, a saturated carbon chain that contains substituents on two of its ends. The number of carbon atoms that are possible in the referenced alkylene group are indicated by the numerical prefix "$C_{n1-n2}$". For example, the term $C_{1-10}$alkylene means an alkylene group having 1, 2, 3, 4, 5, 6, 7, 8, 9 or 10 carbon atoms.

The term "alkenylene" as used herein, whether it is used alone or as part of another group, means straight or branched chain, unsaturated alkenylene group, that is, an unsaturated carbon chain that contains substituents on two of its ends. The number of carbon atoms that are possible in the referenced alkenylene group are indicated by the numerical prefix "$C_{n1-n2}$". For example, the term $C_{2-10}$alkenylene means an alkenylene group having 2, 3, 4, 5, 6, 7, 8, 9 or 10 carbon atoms.

The term "alkynylene" as used herein, whether it is used alone or as part of another group, means straight or branched chain, unsaturated alkynylene group, that is, an unsaturated carbon chain that contains substituents on two of its ends. The number of carbon atoms that are possible in the referenced alkynylene group are indicated by the numerical prefix "$C_{n1-n2}$". For example, the term $C_{2-10}$alkynylene means an alkynylene group having 2, 3, 4, 5, 6, 7, 8, 9 or 10 carbon atoms.

The term "aryl" as used herein, whether it is used alone or as part of another group, refers to cyclic groups that contain at least one aromatic ring. In an embodiment of the present application, the aryl group contains from 6, 9, 10 or 14 atoms, such as phenyl, naphthyl, indanyl or anthracenyl.

The term "heteroaryl" as used herein refers to cyclic groups that contain at least one aromatic ring and at least one heteroatom, such as N, O and/or S. The number of atoms that are possible in the referenced heteroaryl group are indicated by the numerical prefix $C_{n1-n2}$. For example, the term $C_{5-10}$heteroaryl means an aryl group having 5, 6, 7, 8, 9 or 10 atoms, in which at least one atom is a heteroatom, such as N, O and/or S.

The term "cycloalkyl" as used herein, whether it is used alone or as part of another group, means a mono- or bicyclic, saturated alkane group. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms. When a cycloalkyl group contains more than one cyclic structure or rings, the cyclic structures are fused, bridged, spiro connected or linked by a single bond.

A first cyclic structure being "fused" with a second cyclic structure means the first cyclic structure and the second cyclic structure share at least two adjacent atoms therebetween.

A first cyclic structure being "bridged" with a second cyclic structure means the first cyclic structure and the second cyclic structure share at least two non-adjacent atoms therebetween.

A first cyclic structure being "spiro connected" with a second cyclic structure means the first cyclic structure and the second cyclic structure share one atom therebetween.

II. Processes

Processes that include the first enantioselective total synthesis of polyhydroxylated cyclohexenone 1, isolated from *Pleiogynium timorense*, are disclosed herein. Enzymatic dihydroxylation of benzoic acid with *R. eutrophus* B9 provided enantiomerically pure diene diol (1S,6R)-1,6-dihydroxycyclohexa-2,4-dienecarboxylic acid. Elaboration of the carboxylate moiety to the alkyl side chain was followed by singlet oxygen cycloaddition to furnish an endoperoxide whose reduction with thiourea led to cyclitol (3aS,4R,7S,7aR)-3a-((Z)-8,8-dimethoxyoct-1-en-1-yl)-2,2-dimethyl-3a,4,7,7a-tetrahydrobenzo[d][1,3]dioxole-4,7-diol. Several protective operations were used before oxidation and the final extension of the side chain by a Wittig reaction. After final deprotection of the acetonide functionality the desired alkylcyclohexenone 1 was obtained in 14 operations (i.e. 16 total steps when the steps of endoperoxide reduction and acetal deprotection are included) from benzoic acid. The processes of the application are versatile offering many opportunities for modification, for example by using different Wittig reagents and/or post-synthesis modifications, to allow the preparation of derivatives and/or analogs of polyhydroxylated cyclohexyl compounds, such as polyhydroxylated cyclohexenones, including compound 1.

The olefin (3aR,7S,7aR)-3a-((Z)-8,8-dimethoxyoct-1-en-1-yl)-2,2-dimethyl-7-((triisopropylsilyl)oxy)-7,7a-dihydrobenzo[d][1,3]dioxol-4(3aH)-one is a useful intermediate for preparing polyhydroxylated cyclohexenones such as natural products 1-3 and functional analogs thereof.

Accordingly, the present application includes a process for the preparation of a compound of Formula I:

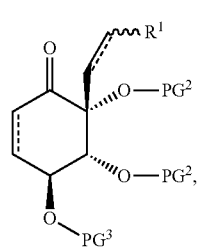

I wherein
both ═══ represent either a single bond or a double bond;
the process comprising:
(a) protecting a compound of Formula II under conditions to provide a compound of Formula III:

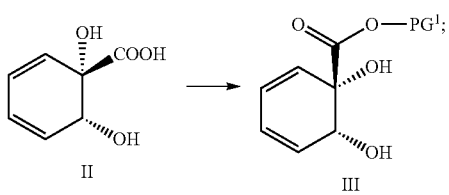

(b) protecting the compound of Formula III under conditions to provide a compound of Formula IV:

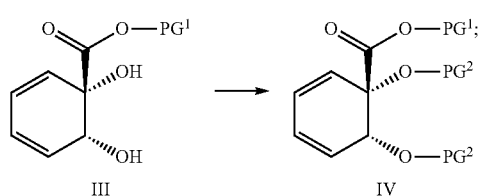

(c) reacting the compound of Formula IV with a first reducing agent under conditions to provide a compound of Formula V:

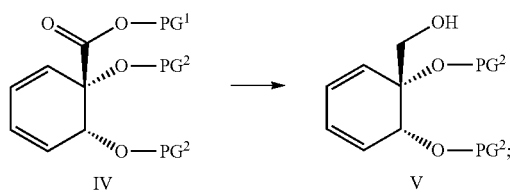

(d) reacting the compound of Formula V with a first oxidizing agent under conditions to provide a compound of Formula VI:

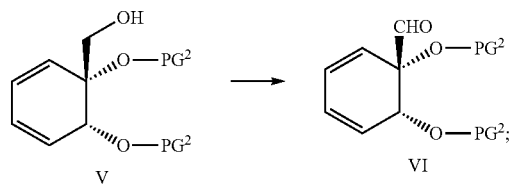

(e) reacting the compound of Formula VI with an alkene-forming reagent of Formula VII under conditions to provide a compound of Formula VIII:

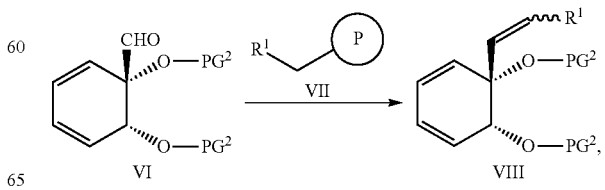

wherein the alkene-forming reagent is a Wittig reagent and

represents a triphenylphosphonium moiety or the alkene-forming reagent is a Horner-Wadsworth-Emmons reagent and

represents a phosphonate moiety;
(f) reacting the compound of Formula VIII with a source of singlet oxygen under conditions to provide an endoperoxide of formula IX:

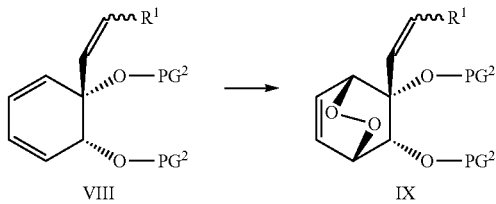

(g) reacting the endoperoxide of Formula IX with a second reducing agent under conditions to provide a compound of Formula X:

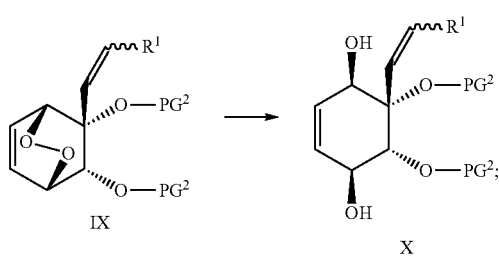

(h-I) when both ===== in the compound of Formula I are a double bond, protecting the compound of Formula X under conditions to provide a compound of Formula XI(i):

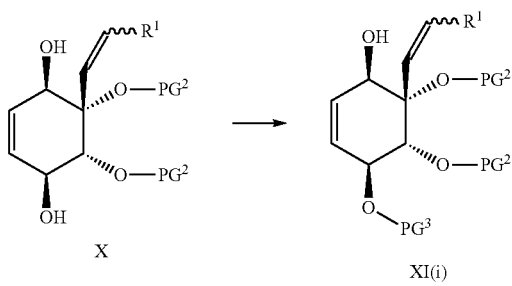

and
(i-I) reacting the compound of Formula XI(i) with a second oxidizing agent under conditions to provide the compound of Formula I, or (h-II) when both ===== in the compound of Formula I are a single bond, hydrogenating the compound of Formula X under conditions to provide a compound of Formula XIX and protecting the compound of Formula XIX under conditions to provide a compound of Formula XI(ii):

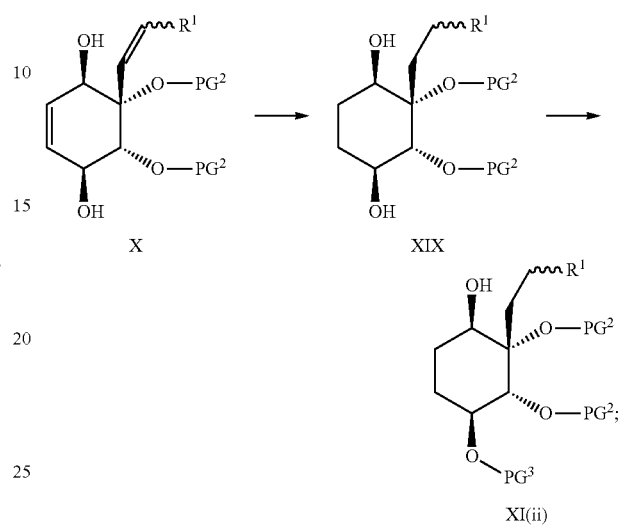

and
(i-II) reacting the compound of Formula XI(ii) with a second oxidizing agent under conditions to provide the compound of Formula I;
wherein
$PG^1$, $PG^2$ and $PG^3$ are each independently protecting groups, wherein $PG^1$ is a protecting group that is removed by the first reducing agent and each $PG^2$ is the same or different or both $PG^2$ are joined to form a cyclic protecting group;
$R^1$ is a functional group that is converted into the functional group of a known natural product or a functional analog thereof; and
wherein in the compounds of Formulae I(i), VII, VIII, IX, X, XI(i), XI(ii) and XIX, one or more available hydrogens in $R^1$ is/are optionally replaced with F and/or one or more of available atoms in $R^1$ is/are optionally replaced with an isotopic label.

The present application also includes a process for the preparation of a compound of Formula I(i):

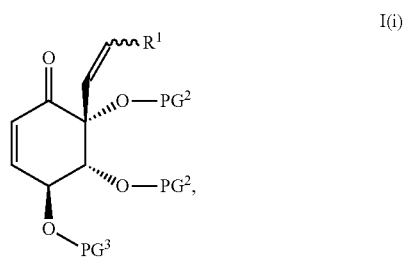

the process comprising:
(a) protecting a compound of Formula II under conditions to provide a compound of Formula III:

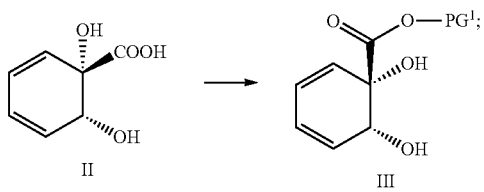

(b) protecting the compound of Formula III under conditions to provide a compound of Formula IV:

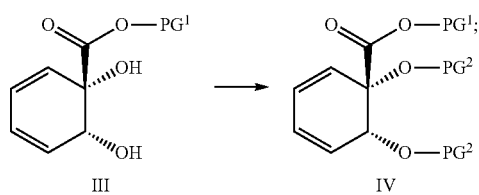

(c) reacting the compound of Formula IV with a first reducing agent under conditions to provide a compound of Formula V:

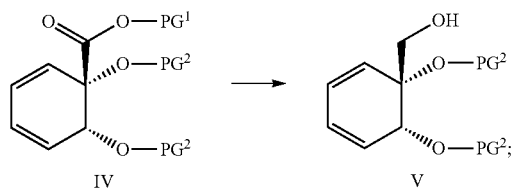

(d) reacting the compound of Formula V with a first oxidizing agent under conditions to provide a compound of Formula VI:

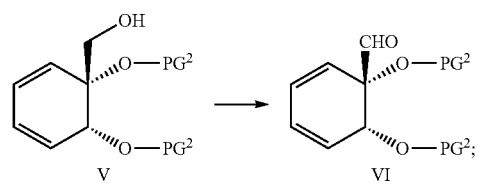

(e) reacting the compound of Formula VI with an alkene-forming reagent of Formula VII under conditions to provide a compound of Formula VIII:

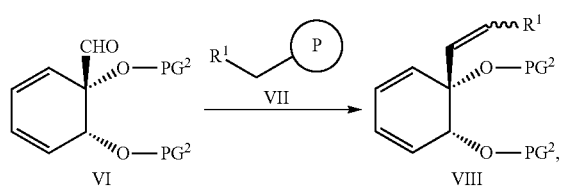

wherein the alkene-forming reagent is a Wittig reagent and

represents a triphenylphosphonium moiety or the alkene-forming reagent is a Horner-Wadsworth-Emmons reagent and

represents a phosphonate moiety;

(f) reacting the compound of Formula VIII with a source of singlet oxygen under conditions to provide an endoperoxide of formula IX:

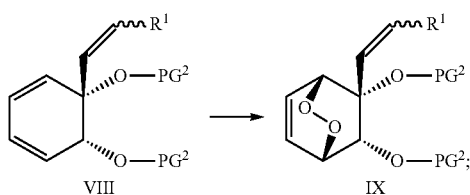

(g) reacting the endoperoxide of Formula IX with a second reducing agent under conditions to provide a compound of Formula X:

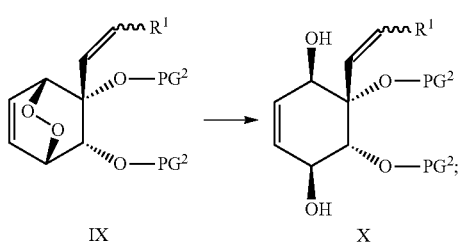

(h) protecting the compound of Formula X under conditions to provide a compound of Formula XI(i):

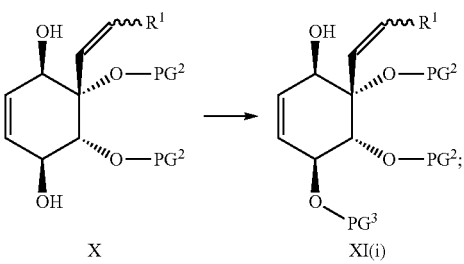

and (i) reacting the compound of Formula XI(i) with a second oxidizing agent under conditions to provide the compound of Formula I(i), wherein $PG^1$, $PG^2$ and $PG^3$ are each independently protecting groups, wherein $PG^1$ is a protecting group that is removed by the first reducing agent and each $PG^2$ is the same or different or both $PG^2$ are joined to form a cyclic protecting group;

$R^1$ is a functional group that is converted into the functional group of a known natural product or a functional analog thereof; and wherein in the compounds of Formulae I(i), VII, VIII, IX, X and XI(i), one or more available hydrogens in $R^1$ is/are optionally replaced with F and/or one or more of available atoms in $R^1$ is/are optionally replaced with an isotopic label.

The present application also includes a process for the preparation of a compound of Formula I(ii):

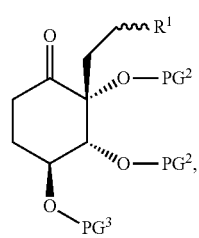

the process comprising:

(a) protecting a compound of Formula II under conditions to provide a compound of Formula III:

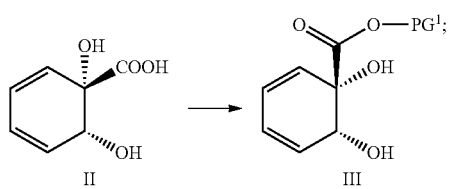

(b) protecting the compound of Formula III under conditions to provide a compound of Formula IV:

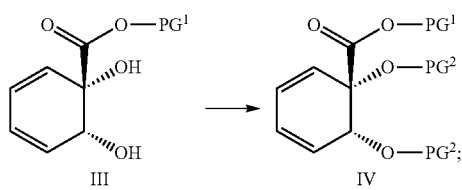

(c) reacting the compound of Formula IV with a first reducing agent under conditions to provide a compound of Formula V:

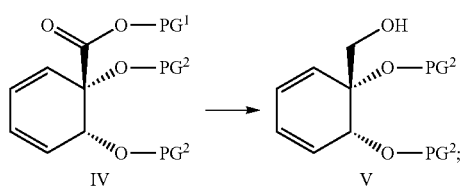

(d) reacting the compound of Formula V with a first oxidizing agent under conditions to provide a compound of Formula VI:

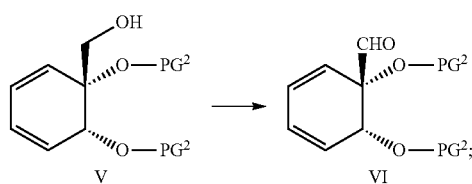

(e) reacting the compound of Formula VI with an alkene-forming reagent of Formula VII under conditions to provide a compound of Formula VIII:

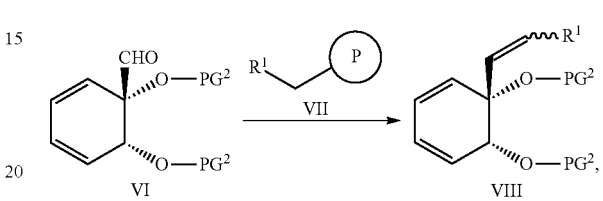

wherein the alkene-forming reagent is a Wittig reagent and

represents a triphenylphosphonium moiety or the alkene-forming reagent is a Horner-Wadsworth-Emmons reagent and

represents a phosphonate moiety;

(f) reacting the compound of Formula VIII with a source of singlet oxygen under conditions to provide an endoperoxide of formula IX:

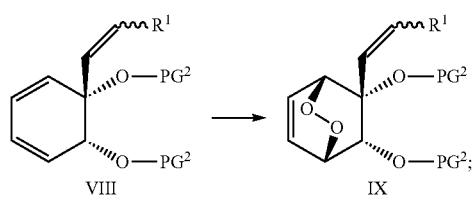

(g) reacting the endoperoxide of Formula IX with a second reducing agent under conditions to provide a compound of Formula X:

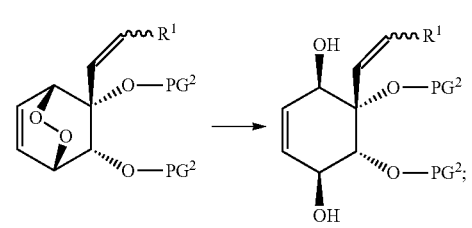

(h) hydrogenating the compound of Formula X under conditions to provide a compound of Formula XIX:

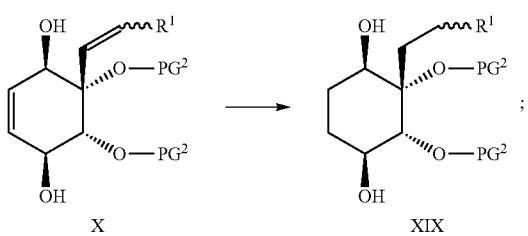

(i) protecting the compound of Formula XIX under conditions to provide a compound of Formula XI(ii):

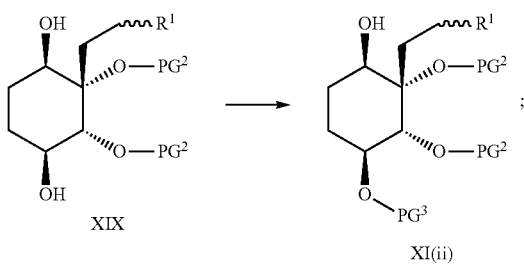

and
(j) reacting the compound of Formula XI(ii) with a second oxidizing agent under conditions to provide the compound of Formula I(ii);
wherein
PG$^1$, PG$^2$ and PG$^3$ are each independently protecting groups, wherein PG$^1$ is a protecting group that is removed by the first reducing agent and each PG$^2$ is the same or different or both PG$^2$ are joined to form a cyclic protecting group;
R$^1$ is a functional group that is converted into the functional group of a known natural product or a functional analog thereof; and
wherein in the compounds of Formulae I(ii), VII, VIII, IX, X, XI(ii) and XIX, one or more available hydrogens in R$^1$ is/are optionally replaced with F and/or one or more of available atoms in R$^1$ is/are optionally replaced with an isotopic label.

Alternatively, in an embodiment, the compound of Formula I(ii) is prepared by a method comprising hydrogenating the compound of Formula I(i) under conditions to provide a compound of Formula I(ii):

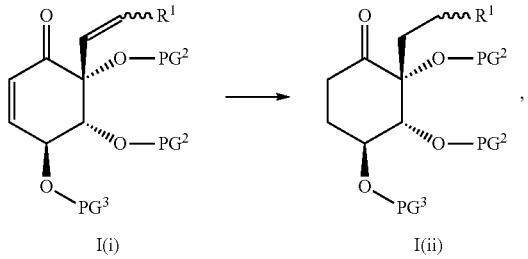

wherein
PG$^2$ and PG$^3$ are each independently protecting groups, wherein each PG$^2$ is the same or different or both PG$^2$ are joined to form a cyclic protecting group;

R$^1$ is a functional group that is converted into the functional group of a known natural product or a functional analog thereof; and
wherein in the compounds of Formulae I(i) and I(ii), one or more available hydrogens in R$^1$ is/are optionally replaced with F and/or one or more of available atoms in R$^1$ is/are optionally replaced with an isotopic label.

In an embodiment of the present application, the alkene-forming reagent is a Wittig reagent, both ===== are a double bond and the compound of Formula I is a compound of Formula I(a):

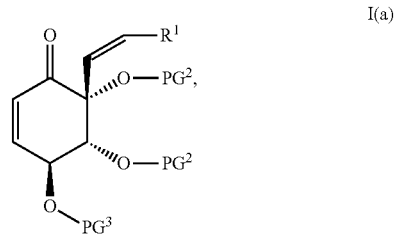

wherein R$^1$ is a functional group that is converted into the functional group of a known natural product or a functional analog thereof; and PG$^2$ and PG$^3$ are each independently protecting groups.

The compound of Formula II is available from known literature methods such as from the fermentation of benzoic acid with *R. eutrophus* B9.$^9$.

The conditions to protect the compound of Formula II to provide the compound of Formula III are any suitable conditions and will depend, for example, on the identity of PG$^1$. The selection of suitable conditions can be made by a person skilled in the art. In an embodiment, PG$^1$ is methyl and the conditions to protect the compound of Formula II to provide the compound of Formula III comprise adding a solution of diazomethane in a suitable solvent such as diethyl ether (for example, diazomethane in a suitable solvent such as diethyl ether obtained via reacting nitrosomethylurea and a suitable base such as KOH in a suitable solvent such as diethyl ether at a temperature of about −5° C. to about 5° C. or about 0° C. for a time for the conversion of the nitrosomethylurea to the diazomethane to proceed to a sufficient extent, for example, about 1 minute to about 10 minutes or about 5 minutes) to a solution of the compound of Formula II in a suitable solvent such as tetrahydrofuran (THF) at a temperature of about −5° C. to about 5° C. or about 0° C., allowing the mixture to warm up to a temperature of about 0° C. to about 30° C. or about room temperature, and stirring for a time for the conversion of the compound of Formula II to the compound of Formula III to proceed to a sufficient extent, for example about 1 hour to about 8 hours or about 4 hours.

The conditions to protect the compound of Formula III to provide the compound of Formula IV are any suitable conditions and will depend, for example, on the identity of PG$^2$. The selection of suitable conditions can be made by a person skilled in the art. In an embodiment, both PG$^2$ are joined to form a cyclic protecting group. In another embodiment of the present application, both PG$^2$ are joined to form —C(CH$_3$)$_2$— and the conditions to protect the compound of Formula III to provide a compound of Formula IV comprise adding a suitable catalyst such as p-TsOH to a solution of the compound of Formula III in 2,2-dimethoxypropane at a temperature of about 0° C. to about 30° C. or about room temperature and stirring for a time for the conversion of the compound of Formula III to the compound of Formula IV to proceed to a sufficient extent, for example, about 1 hour to about 8 hours or about 4 hours.

The first reducing agent is any suitable reducing agent, the selection of which can be made by a person skilled in the art. In an embodiment, the first reducing agent is a metal hydride reducing agent such as $NaBH_4$, $LiAlH_4$, diisobutylaluminum hydride (DIBAL-H) or $LiBH_4$. In another embodiment, the first reducing agent is $LiBH_4$.

The conditions to provide the compound of Formula V are any suitable conditions and will depend, for example, on the identity of the first reducing agent. The selection of suitable conditions can be made by a person skilled in the art. In an embodiment, the first reducing agent is $LiBH_4$ and the conditions to provide the compound of Formula V comprise adding a solution of $LiBH_4$ in a suitable solvent such as THF to a solution of the compound of Formula IV in a suitable solvent such as THF at a temperature of about −5° C. to about 5° C. or about 0° C., stirring for a time of about 30 minutes to about 2 hours or about 1 hour, allowing the mixture to warm up to a temperature of about 0° C. to about 30° C., or about room temperature, and stirring for a time for the conversion of the compound of Formula IV to the compound of Formula V to proceed to a sufficient extent, for example, about 1 hour to about 8 hours, or about 4 hours, at which time the mixture is quenched with a suitable reagent, for example, by addition of ethyl acetate (e.g. dropwise addition) followed by water.

The first oxidizing agent is any suitable oxidizing agent for converting the primary alcohol in the compound of Formula V to the aldehyde in the compound of Formula VI. The selection of a suitable first oxidizing agent can be made by a person skilled in the art. In an embodiment, the oxidation is conducted under mild conditions. In another embodiment, the oxidation is an activated DMSO method such as an oxidation conducted under Swern oxidation conditions. In another embodiment of the present application, the oxidation is a hypervalent iodine method such as a method comprising Dess-Martin periodinane (1,1,1-triacetoxy-1,1-dihydro-1,2-benziodoxol-3(1H)-one), a chromium trioxide method such as a method comprising pyridinium chlorochromate or a method wherein the first oxidizing agent is tetrapropylammonium perruthenate (TPAP) or (2,2,6,6-tetramethylpiperidin-1-yl)oxyl (TEMPO). In a further embodiment, the first oxidizing agent is pyridinium chlorochromate (PCC) and the oxidation is conducted in a suitable solvent such as $CH_2Cl_2$.

The conditions to provide the compound of Formula VI are any suitable conditions and will depend, for example, on the identity of the first oxidizing agent. The selection of suitable conditions can be made by a person skilled in the art. In an embodiment of the present application, the conditions are Swern oxidation conditions. For example, in an embodiment, the conditions to provide the compound of Formula VI comprise adding a solution of the compound of Formula V in a suitable solvent such as $CH_2Cl_2$ to a solution of chloro(dimethyl)sulfonium chloride (for example, a solution of chloro(dimethyl) sulfonium chloride prepared via adding oxalyl chloride to a solution of dimethyl sulfoxide (DMSO) in a suitable solvent, for example $CH_2Cl_2$ at low temperature, for example about −78° C. and allowing the reaction mixture to stir for a time for the conversion of the dimethyl sulfoxide and the oxalyl chloride to the chloro (dimethyl) sulfonium chloride to proceed to a sufficient extent, for example, about 5 minutes to about 30 minutes or about 15 minutes), stirring for a time of about 30 minutes to about 2 hours or about 1 hour, and stirring while allowing the mixture to warm up to a temperature of about 0° C. to about 30° C. or about room temperature over a time for the conversion of the compound of Formula V to the compound of Formula VI to proceed to a sufficient extent, for example, about 6 hours to about 24 hours or about 12 hours, at which time the mixture is quenched with a suitable reagent, for example, water (e.g. by pouring the mixture into the water).

A person skilled in the art can select a suitable alkene-forming reagent to provide the desired isomerism at the double bond of the compound of Formula VIII. For example, it will be appreciated by a person skilled in the art that the Horner-Wadsworth-Emmons reaction produces predominately E-alkenes whereas a typical Wittig reaction produces predominately Z-alkenes.

In an embodiment, the alkene-forming reagent of Formula VII is a Wittig reagent. In another embodiment of the present application, the alkene-forming reagent of Formula VII is a Horner-Wadsworth-Emmons reagent.

The conditions to provide the compound of Formula VIII are any suitable conditions and will depend, for example, on the alkene-forming reagent used. The selection of suitable conditions can be made by a person skilled in the art. The desired Wittig reagent (triphenyl phosphonium ylide) or Horner-Wadsworth-Emmons reagent of Formula VII can be prepared by standard means known in the art (see, for example, ref. 14 for preparation of an exemplary Wittig reagent). In an embodiment, the alkene-forming reagent is a Wittig reagent and the conditions to provide the compound of Formula VIII comprise adding a solution of n-butyl lithium in a suitable solvent to a solution of the Wittig reagent of Formula VII in a suitable solvent such as THF at low temperature, for example about −78° C., stirring for a time of about 5 minutes to about 30 minutes or about 15 minutes, allowing the mixture to warm up to a temperature of about 0° C. to about 30° C. or about room temperature, cooling the mixture to low temperature, for example, about −78° C., adding the compound of Formula VI, stirring for a time for the conversion of the compound of Formula VI to the compound of Formula VIII to proceed to a sufficient extent, for example, about 1 hour to about 6 hours or about 3 hours, and allowing the mixture to warm up to a temperature of about 0° C. to about 30° C. or about room temperature, at which time the mixture is quenched with a suitable reagent, for example, $NH_4Cl$, for example, added in the form of a saturated aqueous solution.

The conditions to provide the endoperoxide of Formula IX are any suitable conditions and will depend, for example, on the identity of the source of singlet oxygen. The selection of suitable conditions can be made by a person skilled in the art. In an embodiment, the source of singlet oxygen for the conversion of the compound of Formula VIII to the compound of Formula IX is that provided using well-known photooxidation procedures (see, for example, CRC Handbook of Organic Photochemistry and Photobiology, Ed. William Horspool and Francesco Lenci, CRC Press, 2004). For example, using tetraphenylporphyrin (TPP), Rose Bengal, methylene blue or a porphyrin, or polymer-supported versions thereof, and oxygen gas in the presence of irradiation. Suitable solvents and reaction temperatures and reactant ratios are selected using known methods by a person skilled in the art. Accordingly, the compound of Formula VIII is dissolved in a suitable solvent or mixture of solvents and photo-oxygenated, for example, by adding a photosensitizer and bubbling oxygen through the reaction mixture for several hours, while irradiating the mixture (e.g., with a lamp having a power output of about 10 W to about 5000 W, depending on the sensitizer, for example having a power output of about 500 W) to provide the endoperoxide IX. Examples of solvents useful in the photo-oxygenation reaction include, but are not limited to, alcohols (e.g., methanol (MeOH), ethanol (EtOH), isopropanol, butanol (BuOH), 1-octanol), chloroform, tetrachloromethane ($CCl_4$), dichloromethane ($CH_2Cl_2$ or DCM), N-methyl-2-pyrrolidone (NMP), acetonitrile, dimethylformamide (DMF), morpholine, hexamethylphosphoramide (HMPA), nitromethane, acetone, dioxane, 3-butanone, toluene, dimethyl sulfoxide (DMSO), naphthalene, dimethylbenzamide, ionic liquids (e.g., ethylammonium nitrate, 3-methylimidazolium (BMIM) salt), fluorous phase, or any aliphatic, heteroaliphatic, heterocyclic (ring size 3-10 atoms), or carbocyclic (ring size 3-10 atoms) solvents, or mixtures thereof. In one embodiment, a mixture of a chlorinated solvent (e.g., chloroform, DCM) and an alcohol (e.g., MeOH, EtOH, isopropanol, BuOH, 1-octanol) is used. In a further embodiment, a mixture of DCM and MeOH is used. In another embodiment, DCM is used. In an embodiment, the photo-oxygenation reaction is run at a temperature of about −40° C. to about 80° C., in a particular embodiment about 5° C. to about 15° C. and the mixture stirred for a time for the conversion of the compound of Formula VIII to the compound of Formula IX to proceed to a sufficient extent, for example a time of about 12 hours to about 4 days or about 40 hours. In a further embodiment, alternative sources of singlet oxygen are used, for example that described in Nardello, Veronique et al. *Lanthanum(III)-catalyzed disproportionation of hydrogen peroxide: a heterogeneous generator of singlet molecular oxygen —$^1O_2$ (1D g)-in near-neutral aqueous and organic media for peroxidation of electron-rich substrates*. Chemistry-A European Journal (2003), 9(2), 435-441.

The second reducing agent is any suitable reducing agent for the reduction of the endoperoxide in the compound of Formula IX to the diol in the compound of Formula X, the selection of which can be made by a person skilled in the art. In an embodiment, the second reducing agent is a thiourea, a metal hydride, a phosphine, a Hg/Al amalgam or $Mo(CO)_6$. In another embodiment of the present application, the second reducing agent is a thiourea.

The conditions to provide the compound of Formula X are any suitable conditions and will depend, for example, on the identity of the second reducing agent. The selection of suitable conditions can be made by a person skilled in the art. In an embodiment, the second reducing agent is thiourea and the conditions to provide the compound of Formula X comprise adding a solution of the thiourea in a suitable solvent such as methanol (for example, via dropwise addition over about 10 minutes to about 30 minutes or about 20 minutes, while stirring the resulting mixture) to a solution of the compound of Formula IX in a suitable solvent such as $CH_2Cl_2$ at a temperature of about 0° C. to about 30° C. or about room temperature and stirring for a time for the conversion of the compound of Formula IX to the compound of Formula X to proceed to a sufficient extent, for example about 30 minutes to about 3 hours or about 1.5 hours.

The conditions to protect the compound of Formula X to provide the compound of Formula XI(i) or to protect the compound of Formula XIX to provide the compound of Formula XI(ii) are any suitable conditions and will depend, for example, on the identity of $PG^3$. The selection of suitable conditions can be made by a person skilled in the art. For example, the skilled person would appreciate that the steric hindrance at the top portion of the compound of Formula X can be used in the selective protection of the less hindered alcohol and will select $PG^3$ and the conditions accordingly. In an embodiment, $PG^3$ is triisopropylsilane triflyl and the conditions to provide the compound of Formula XI(i) or XI(ii) comprise adding triisopropylsilane triflate (for example, via dropwise addition over about 1 minute to about 10 minutes or about 5 minutes, while stirring) to a solution of the compound of Formula X or the compound of Formula XIX, as the case may be, and a suitable base such as a sterically hindered mild base, for example, 2,6-lutidine (2,6-dimethylpyridine) in a suitable solvent such as $CH_2Cl_2$ at a low temperature, for example about −78° C., and stirring while allowing the mixture to warm up to a temperature of about 0° C. to about 30° C. or about room temperature over a time for the conversion of the compound of Formula X to the compound of Formula XI(i) or the conversion of the compound of Formula XIX to the compound of Formula XI(ii) to proceed to a sufficient extent, for example, about 1 hour to about 6 hours or about 3 hours, at which time the mixture is quenched with a suitable reagent such as $NH_4Cl$, for example, added in the form of a saturated aqueous solution. In an embodiment, the undesired regioisomer side product (i.e. the compound wherein the other alcohol is protected) is recycled by a process comprising deprotection and reprotection.

The second oxidizing agent is any suitable oxidizing agent for converting the secondary alcohol in the compound of Formula XI(i) or XI(ii) to the ketone in the compound of Formula I. The selection of a suitable second oxidizing agent can be made by a person skilled in the art. In an embodiment, the oxidation is an activated DMSO method such as an oxidation conducted under Swern conditions, a hypervalent iodine method such as a method comprising Dess-Martin periodinane (1,1,1-triacetoxy-1,1-dihydro-1,2-benziodoxol-3(1H)-one), a chromium trioxide method such as a method comprising pyridinium chlorochromate or a method wherein the second oxidizing agent is tetrapropylammonium perruthenate (TPAP) or (2,2,6,6-tetramethylpiperidin-1-yl)oxyl (TEMPO). In another embodiment of the present application, the second oxidizing agent is a periodinane such as 2-iodoxybenzoic acid (IBX).

The conditions to hydrogenate the compound of Formula X to provide the compound of Formula XIX or the compound of Formula I(ii) from the compound of Formula I(i) are any suitable conditions and will depend, for example, on the identity of the hydrogenating agent. The selection of suitable conditions can be made by a person skilled in the art. In an embodiment, the conditions to provide the compound of Formula XIX from the compound of Formula X or the compound of Formula I(ii) from the compound of Formula I(i), comprise any of the known methods for the hydrogenation of compounds, including for example, transfer hydrogenation, or the use of hydrogen gas in the presence of a catalyst, such as Pd/C or any of the well-known transition metal hydrogenation catalysts or by the use of diimide. Suitable solvents and reaction temperatures and reactant ratios are selected using known methods by a person skilled in the art. In an embodiment, the conditions to provide the compound of Formula XIX from the compound of Formula X or the compound of Formula I(ii) from the compound of Formula I(i), comprise dissolving the compound of Formula X or the compound of Formula I(i) in a solvent or mixture of solvents with or without acid in the presence of a suitable hydrogenation catalyst. Examples of suitable acids include, for example, HCl, HBr, HI, $H_2SO_4$ and any other mineral acid, or any organic acids such as formic acid or acetic acid, or a mixture thereof. Examples of suitable hydrogenation catalysts include, for example, Pd, Pd(II), Pt, Rh and Ir and their derivatives. In a further embodiment, the reaction mixture is treated with hydrogen (for example at 1 atm or any other suitable pressures) at a temperature of about 0° C. to about 100° C. until complete consumption of the starting material has occurred. Examples of solvents useful in the hydrogenation reaction include, for example, alcohols, such as MeOH, EtOH, isopropanol, BuOH and 1-octanol, water, aqueous solutions of mineral acids and aqueous organic acids, such as formic acid and acetic acid, and mixtures thereof. In an embodiment, the conditions to provide the compound of Formula XIX or the compound of Formula I(ii) comprise adding Wilkinson's catalyst to a solution of the compound of Formula X or the compound of Formula I(i) as the case may be, in a suitable solvent such as methanol and allowing the solution to stir at a temperature of about 0° C. to about 30° C. or room temperature in the presence of $H_2$, for example about 1 atm (or any other suitable pressure) of $H_2$ for a time for the conversion of the compound of Formula X to the compound of Formula XIX or the compound of Formula I(i) to the compound of Formula I(ii) to proceed to a sufficient extent, for example, about 12 hours to about 48 hours or about 20 hours. It will also be appreciated by a person skilled in the art that a hydrogenation to prepare a dihydropleiogenone, a derivative thereof and/or a precursor thereto can also, for example, occur at other suitable steps in the processes of the present application. For example, in some embodiments, the hydrogenation is of a compound of Formula XI or a similar compound to provide the corresponding desired saturated compound. The conditions to hydrogenate such a compound to provide the corresponding saturated compound are any suitable conditions and will depend, for example, on the identity of the hydrogenating agent. The selection of suitable conditions can be made by a person skilled in the art.

The conditions to provide the compound of Formula I from the compound of Formula XI(i) or XI(ii) are any suitable conditions and will depend, for example, on the identity of the second oxidizing agent. The selection of suitable conditions can be made by a person skilled in the art. In an embodiment, the second oxidizing agent is 2-iodoxybenzoic acid (IBX) and the conditions to provide the compound of Formula I comprise adding IBX (for example, adding IBX portionwise) to a solution of the compound of Formula XI(i) or XI(ii) in a suitable solvent such as ethyl acetate, heating the mixture to the reflux temperature of the solvent, and refluxing the mixture for a time for the conversion of the compound of Formula XI(i) or XI(ii) to the compound of Formula I to proceed to a sufficient extent, for example, about 1 hour to about 8 hours or about 4 hours.

In an embodiment, the conversion of the

into the functional group of a known natural product or a functional analog thereof comprises hydrogenation of the olefin in the

moiety.

Accordingly, the present application also includes a process for the preparation of a compound of Formula XII:

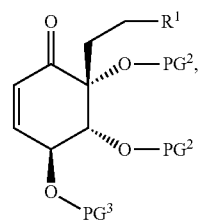

the process comprising:
(a) protecting a compound of Formula I(i) under conditions to provide a compound of Formula XIII:

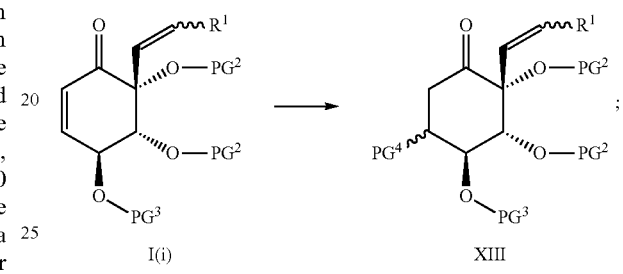

(b) hydrogenating the compound of Formula XIII under conditions to provide a compound of Formula XIV:

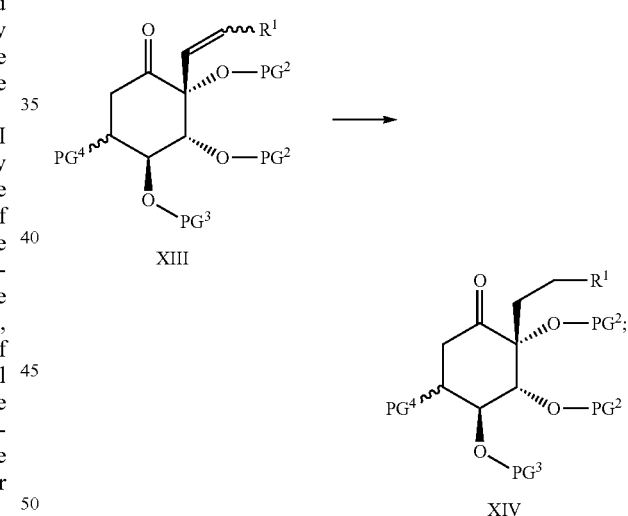

and
(c) deprotecting the compound of Formula XIV under conditions to remove $PG^4$ and provide the compound of Formula XII,
wherein
$PG^2$ and $PG^3$ are each independently protecting groups;
and $R^1$ is a functional group that is converted into the functional group of a known natural product or a functional analog thereof;
$PG^4$ is a protecting group; and
wherein in the compounds of Formulae I(i), XII, XIII and XIV, one or more available hydrogens in $R^1$ is/are optionally replaced with F and/or one or more of available atoms in $R^1$ is/are optionally replaced with an isotopic label.

The conditions to protect of the compound of Formula I(i) to provide the compound of Formula XIII are any suitable conditions and will depend, for example, on the identity of PG$^4$. The selection of PG$^4$ and suitable conditions can be made by a person skilled in the art. In an embodiment, the compound of Formula XIII is a thioadduct and the conditions to protect the compound of Formula I(i) to provide the compound of Formula XIII comprise adding thiophenol and a suitable base such as triethylamine to a solution of the compound of Formula I in a suitable solvent such as CH$_2$Cl$_2$ at a temperature of about 0° C. to about 30° C. or about room temperature, and stirring for a time for the conversion of the compound of Formula I to the compound of Formula XIII to proceed to a sufficient extent, for example, about 6 hours to about 24 hours or about 12 hours.

The conditions to hydrogenate the compound of Formula XIII to provide the compound of Formula XIV are any suitable conditions and will depend, for example, on the identity of the hydrogenating agent. The selection of suitable conditions can be made by a person skilled in the art. In an embodiment, the conditions to provide the compound of Formula XIV from the compound of Formula XIII, comprise any of the known methods for the hydrogenation of compounds, including for example, transfer hydrogenation, or the use of hydrogen gas in the presence of a catalyst, such as Pd/C or any of the well-known transition metal hydrogenation catalysts or by the use of diimide. Suitable solvents and reaction temperatures and reactant ratios are selected using known methods by a person skilled in the art. In an embodiment, the conditions to provide the compound of Formula XIV from the compound of Formula XIII, comprise dissolving the compound of Formula XIII in a solvent or mixture of solvents with or without acid in the presence of a suitable hydrogenation catalyst. Examples of suitable acids include, for example, HCl, HBr, HI, H$_2$SO$_4$ and any other mineral acid, or any organic acids such as formic acid or acetic acid, or a mixture thereof. Examples of suitable hydrogenation catalysts include, for example, Pd, Pd(II), Pt, Rh and Ir and their derivatives. In a further embodiment, the reaction mixture is treated with hydrogen (for example at 1 atm or any other suitable pressures) at a temperature of about 0° C. to about 100° C. until complete consumption of the starting material has occurred. Examples of solvents useful in the hydrogenation reaction include, for example, alcohols, such as MeOH, EtOH, isopropanol, BuOH and 1-octanol, water, aqueous solutions of mineral acids and aqueous organic acids, such as formic acid and acetic acid, and mixtures thereof. In an embodiment, the conditions to provide the compound of Formula XIV comprise adding Wilkinson's catalyst to a solution of the compound of Formula XIII in a suitable solvent such as methanol and allowing the solution to stir at a temperature of about 0° C. to about 30° C. or room temperature in the presence of H$_2$, for example about 1 atm (or any other suitable pressure) of H$_2$ for a time for the conversion of the compound of Formula XIII to the compound of Formula XIV to proceed to a sufficient extent, for example, about 12 hours to about 48 hours or about 20 hours.

The conditions to deprotect the compound of Formula XIV to provide the compound of Formula XII are any suitable conditions. The selection of suitable conditions can be made by a person skilled in the art. In an embodiment, the conditions to provide the compound of Formula XII from the compound of Formula XIV comprise adding a suitable non-nucleophilic base such as 1,8-diazabicycloundec-7-ene (DBU) to a solution of the compound of Formula XIV in a suitable solvent such as CH$_2$Cl$_2$ at a temperature of about 0° C. to about 30° C. or room temperature, and stirring for a time for the conversion of the compound of Formula XIV to the compound of Formula XII to proceed to a sufficient extent, for example about 4 hours to about 16 hours or about 8 hours.

In an embodiment, the functional group of a known natural product or analog thereof is C$_{1-20}$alkyl, C$_{2-20}$akenyl or C$_{2-20}$alkynyl and therefore R$^1$ is any functional group that is converted, using known chemistries, to these groups. In an embodiment, the functional group of a known natural product or analog thereof is C$_{6-20}$alkyl, C$_{6-20}$akenyl or C$_{6-20}$alkynyl. In an embodiment, the C$_{6-20}$akenyl or C$_{6-20}$alkynyl groups of the functional group of a known natural product or analog thereof comprises 1 or 2 double or triple bonds. In an embodiment, the C$_{6-20}$akenyl or C$_{6-20}$alkynyl groups of the functional group of a known natural product or analog thereof comprises 1 double or triple bond. In an embodiment, the C$_{6-20}$akenyl or C$_{6-20}$alkynyl groups of the functional group of a known natural product or analog thereof comprises 1 double. In an embodiment, the functional group of a known natural product or analog thereof is

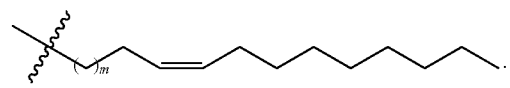

wherein m is 5, 7 or 9.

In some embodiments, the functional group that is converted to a functional group of a known natural product or analog thereof (R$^1$) comprises a terminal aldehyde or a protected form thereof. In some embodiments, the functional group that is converted to a functional group of a known natural product or analog thereof (R$^1$) comprises a terminal aldehyde or an acetal, for example, a suitable cyclic acetal such as ethylene glycol acetal or a suitable acyclic acetal such as —C(OMe)$_2$.

In an embodiment, the compound of Formula XII is a compound of Formula XII(a):

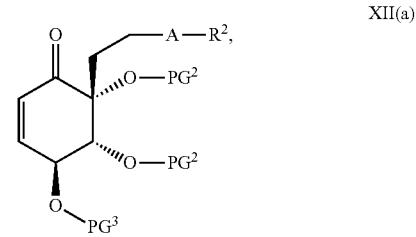

XII(a)

wherein
PG$^2$ and PG$^3$ are each independently protecting groups;
A is C$_{1-20}$alkylene;
R$^2$ is a functional group that is converted into an aldehyde; and
wherein in the compound of Formula XII(a), one or more available hydrogens in A and R$^2$ is/are optionally replaced with F and/or one or more of available atoms in A and R$^2$ is/are optionally replaced with an isotopic label.

In an embodiment, A is C$_{1-12}$alkylene. In another embodiment, A is C$_{3-12}$alkylene. In a further embodiment, A is —(CH$_2$)$_m$—, wherein m is 5, 7 or 9. it is an embodiment that A is —(CH$_2$)$_m$—, wherein m is 5. In another embodiment, A is —(CH$_2$)$_m$—, wherein m is 7. In a further embodiment, A is —(CH$_2$)$_m$—, wherein m is 9.

Accordingly, the present application also includes a process for the preparation of a compound of Formula XV(i):

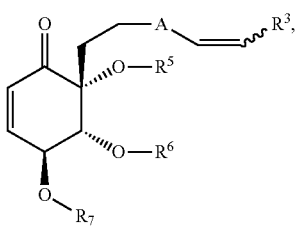

XV(i)

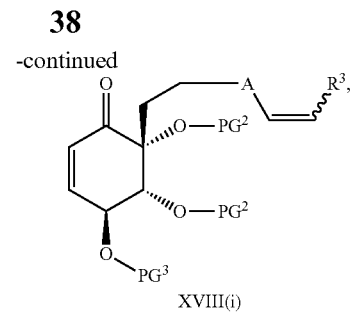

XVIII(i)

wherein

A is $C_{1-20}$alkylene;

$R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups; and $R^5$, $R^6$ and $R^7$ are each independently H, $C_{1-6}$alkyl or aryl, the process comprising:

(a) reacting a compound of Formula XII(a) under conditions to convert $R^2$ into an aldehyde to provide a compound of Formula XVI(i):

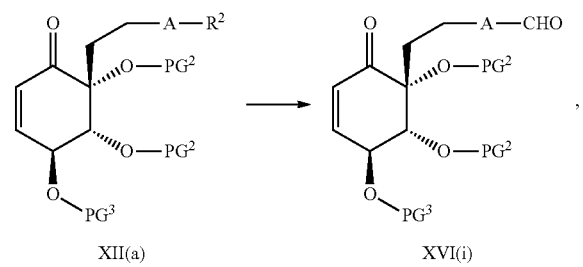

wherein

A is $C_{1-20}$alkylene;

$R^2$ is a functional group that is converted into an aldehyde; and $PG^2$ and $PG^3$ are each independently protecting groups; and (b) reacting the compound of Formula XVI(i) with an alkene-forming reagent of Formula XVII under conditions to provide a compound of Formula XVII(i):

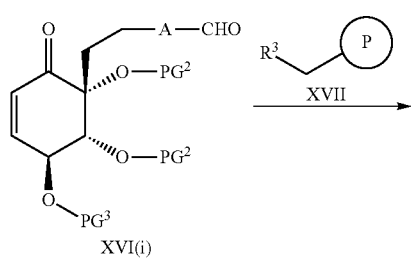

wherein the alkene-forming reagent is a Wittig reagent and (P)

represents a triphenylphosphonium moiety or the alkene-forming reagent is a Horner-Wadsworth-Emmons reagent and (P)

represents a phosphonate moiety;

A is C1-20alkylene;

$PG^2$ and $PG^3$ are each independently protecting groups; and $R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups;

(c) deprotecting the compound of Formula XVIII(i) under conditions to provide the compound of Formula XV(i) wherein $R^5$, $R^6$ and $R^7$ are all H; and (d) optionally reacting the compound of Formula XV(i) wherein $R^5$, $R^6$ and $R^7$ are all H under conditions to convert one or more of $R^5$, $R^6$ and $R^7$ to $C_{1-6}$alkyl or aryl, wherein in the compounds of Formulae XII(a), XV(i), XVI(i), XVII and XVII(i), one or more available hydrogens in A, $R^2$ and/or $R^3$ is/are optionally replaced with F and/or one or more of available atoms in A, $R^2$ and/or $R^3$ is/are optionally replaced with an isotopic label.

The present application also includes a process for the preparation of a compound of Formula XV(ii):

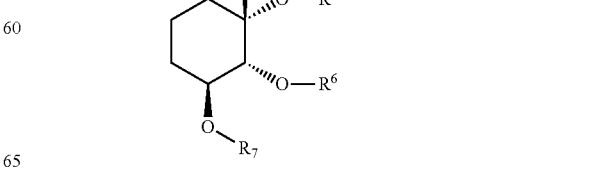

wherein

A is as $C_{1-20}$alkylene;

$R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups; and $R^5$, $R^6$ and $R^7$ are each independently H, $C_{1-6}$alkyl or aryl, the process comprising:

(a) reacting a compound of Formula I(ii) under conditions to convert $R^2$ into an aldehyde to provide a compound of Formula XVI(ii):

[Structure I(ii) → Structure XVI(ii)]

wherein

A is $C_{1-20}$alkylene, $R^2$ is a functional group that is converted into an aldehyde; and $PG^2$ and $PG^3$ are each independently protecting groups; and (b) reacting the compound of Formula XVI(ii) with an alkene-forming reagent of Formula XVII(ii) under conditions to provide a compound of Formula XVIII(ii):

[Structure XVI(ii) + XVII → Structure XVIII(ii)]

wherein the alkene-forming reagent is a Wittig reagent and (P) represents a triphenylphosphonium moiety or the alkene-forming reagent is a Horner-Wadsworth-Emmons reagent and (P) represents a phosphonate moiety;

A is $C_{1-20}$alkylene;

$PG^2$ and $PG^3$ are each independently protecting groups; and $R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups;

(c) deprotecting the compound of Formula XVIII(ii) under conditions to provide the compound of Formula XV(ii) wherein $R^5$, $R^6$ and $R^7$ are all H; and (d) optionally reacting the compound of Formula XV(ii) wherein $R^5$, $R^6$ and $R^7$ are all H under conditions to convert one or more of $R^5$, $R^6$ and $R^7$ to $C_{1-6}$alkyl or aryl, wherein in the compounds of Formulae I(ii), XV(ii), XVI(ii), XVII and XVIII(ii), one or more available hydrogens in A, $R^2$ and/or $R^3$ is/are optionally replaced with F and/or one or more of available atoms in A, $R^2$ and/or $R^3$ is/are optionally replaced with an isotopic label.

Alternatively, in an embodiment, the compound of Formula XV(ii) is prepared by a process comprising hydrogenating the compound of Formula XV(i) under conditions to provide a compound of Formula XV(ii):

[Structure XV(i) → Structure XV(ii)]

wherein

A is $C_{1-20}$alkylene;

$R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups; and $R^5$, $R^6$ and $R^7$ are each independently H, $C_{1-6}$alkyl or aryl.

The conditions to hydrogenate the compound of Formula XV(i) to provide the compound of Formula XV(ii) are any suitable conditions and will depend, for example, on the identity of the hydrogenating agent. The selection of suitable conditions can be made by a person skilled in the art. For example, in some embodiments, the enone in pleiogenone or a derivative thereof of the Formula XV(i) is reduced by a hydride in the presence of Stryker's reagent ([(PPh$_3$)CuH]$_6$).

In some embodiments, R$^2$ is any suitable functional group that can be converted into an aldehyde, the selection of which can be made by a person skilled in the art. In an embodiment, R$^2$ is an acetal, for example, a suitable cyclic acetal such as ethylene glycol acetal or a suitable acyclic acetal such as —C(OMe)$_2$.

The conditions to convert R$^2$ in the compound of Formula XII(a) or Formula I(ii) into an aldehyde to provide a compound of Formula XVI(i) or Formula XVI(ii), respectively, can be any suitable conditions and will depend, for example, on the identity of R$^2$. The selection of suitable conditions can be made by a person skilled in the art. For example, it will be appreciated by a person skilled in the art that when R$^2$ is an acetal, conditions to provide the aldehyde of the compound of Formula XVI(i) or Formula XV(ii) comprise the selective hydrolysis of the acetal of the compound of Formula XII(a) or Formula I(ii), respectively. In an embodiment, R$^2$ is —C(OMe)$_2$ and the conditions to provide the compound of Formula XVI(i) or Formula XV(ii) comprise adding the compound of Formula XII(a) or Formula I(ii), respectively to a solution of iodine in a suitable solvent such as acetone at a temperature of about 0° C. to about 30° C. or room temperature and stirring for a time for the conversion of the compound of Formula XII(a) to the compound of Formula XVI(i) or the conversion of the compound of Formula I(ii) to the compound of Formula XVI(ii) to proceed to a sufficient extent, for example, about 5 minutes to about 20 minutes or about 10 minutes, followed by quenching with a suitable reagent such as sodium thiosulfate (Na$_2$S$_2$O$_3$), for example, added in the form of an about 5% aqueous solution.

A person skilled in the art can select a suitable alkene-forming reagent to provide the desired isomerism at the double bond of the compound of Formula XVII(i) or Formula VXIII(ii). For example, it will be appreciated by a person skilled in the art that the Horner-Wadsworth-Emmons reaction produces predominately E-alkenes whereas a typical Wittig reaction produces predominately Z-alkenes.

In an embodiment, the alkene-forming reagent of Formula XVII is a Wittig reagent. In another embodiment of the present application, the alkene-forming reagent of Formula VII is a Horner-Wadsworth-Emmons reagent.

The conditions to provide the compound of Formula XVIII(i) or Formula XVIII(ii) are any suitable conditions and will depend, for example, on the alkene-forming reagent used. The selection of suitable conditions can be made by a person skilled in the art. The desired Wittig reagent (triphenyl phosphonium ylide) or Horner-Wadsworth-Emmons reagent of Formula XVII can be prepared by standard means known in the art (see, for example, ref. 14 for preparation of an exemplary Wittig reagent). In an embodiment, the alkene-forming reagent is a Wittig reagent and the conditions to provide the compound of Formula XVII(i) or Formula XVIII(ii) comprise adding a solution of n-butyl lithium in a suitable solvent to a solution of the Wittig reagent of Formula XVII in a suitable solvent such as THF at low temperature, for example about −78° C., stirring for a time of about 5 minutes to about 30 minutes or about 15 minutes, allowing the mixture to warm up to a temperature of about 0° C. to about 30° C. or about room temperature, cooling the mixture to low temperature, for example, about −78° C., adding the compound of Formula XVI(i) or Formula XVI (ii), stirring for a time for the conversion of the compound of Formula XVI(i) to the compound of Formula XVIII(ii) or the conversion of the compound of Formula XVI(ii) to the compound of Formula XVIII(ii) to proceed to a sufficient extent, for example, about 1 hour to about 6 hours or about 3 hours, and allowing the mixture to warm up to a temperature of about 0° C. to about 30° C. or about room temperature, at which time the mixture is quenched with a suitable reagent, for example, NH$_4$Cl, for example, added in the form of a saturated aqueous solution.

In an embodiment, R$^3$ is C$_{1-12}$alkyl, C$_{2-12}$alkenyl, C$_{2-12}$alkynyl, C$_{1-10}$alkylene-R$^4$, C$_{2-10}$alkenylene-R$^4$ or C$_{2-10}$alkynylene-R$^4$, wherein R$^4$ is C$_{3-6}$cycloalkyl or phenyl, and wherein the C$_{1-12}$alkyl, C$_{2-12}$alkenyl, C$_{2-12}$alkynyl, C$_{1-10}$alkylene, C$_{2-10}$alkenylene or C$_{2-10}$alkynylene is optionally substituted with one or more hydroxy groups. In another embodiment, R$^3$ is C$_{1-12}$alkyl, C$_{2-12}$alkenyl, C$_{1-10}$alkylene-R$^4$ or C$_{2-10}$alkenylene-R$^4$ wherein R$^4$ is C$_{3-6}$cycloalkyl or phenyl, and wherein the C$_{1-12}$alkyl, C$_{2-12}$alkenyl, C$_{1-10}$alkylene or C$_{2-10}$alkenylene is optionally substituted with one or more hydroxy groups. In a further embodiment, R$^3$ is C$_{1-12}$alkyl or C$_{2-12}$alkenyl, wherein the C$_{1-12}$alkyl or C$_{2-12}$alkenyl is optionally substituted with one or more hydroxy groups. It is an embodiment that R$^3$ is C$_{1-12}$alkyl. In another embodiment, R$^3$ is C$_{6-10}$ alkyl. In a further embodiment, R$^3$ is octyl.

In an embodiment, R$^3$ is a C$_{2-20}$alkynyl group, wherein the alkynyl moiety is a terminal alkynyl moiety (i.e. is at the distal end of R$^3$). In another embodiment, R$^3$ is C$_2$-C$_{12}$alkylene-C≡CH. In a further embodiment, R$^3$ is C$_4$-C$_8$alkylene-C≡CH. It is an embodiment that R$^3$ is (CH$_2$)$_6$—C≡CH.

The conditions to deprotect the compound of Formula XVIII(i) or Formula XVIII(ii) to provide the compound of Formula XV(i) or Formula XV(ii), wherein R$^5$, R$^6$ and R$^7$ are all H can be any suitable conditions. The selection of suitable conditions can be made by a person skilled in the art. In an embodiment, the conditions to provide the compound of Formula XV(i) or Formula XV(ii), wherein R$^5$, R$^6$ and R$^7$ are all H comprise adding the compound of Formula XVII(i) or Formula XVII(ii) to a solution of iodine in a suitable solvent such as acetonitrile at a temperature of about 0° C. to about 30° C. or room temperature and stirring for a time for the conversion of the compound of Formula XVII(i) to the compound of Formula XV(i) or the conversion of the compound of Formula XVIII(ii) to the compound of Formula XV(ii), wherein R$^5$, R$^6$ and R$^7$ are all H to proceed to a sufficient extent, for example, about 4 hours to about 24 hours or about 10 hours, optionally diluting the mixture with a suitable solvent such as CH$_2$Cl$_2$ and quenching with a suitable reagent such as sodium thiosulfate (Na$_2$S$_2$O$_3$), for example, added in the form of an about 5% aqueous solution.

In an embodiment, the compound of Formula XV is a compound of Formula XV(a):

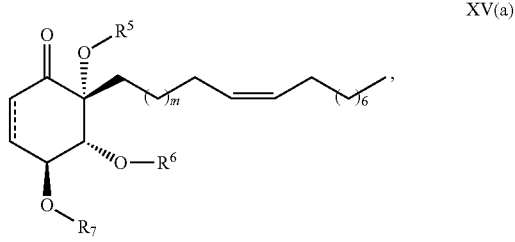

wherein

===== represents either a single bond or a double bond;

m is 5, 7 or 9; and $R^5$, $R^6$ and $R^7$ are each independently H, $C_{1-6}$alkyl or aryl.

In an embodiment, the compound of Formula XV(a) is a compound of Formula XV(a)(i):

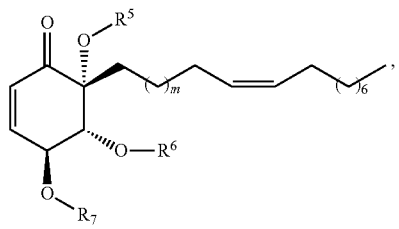

XV(a)(i)

wherein m is 5, 7 or 9; and $R^5$, $R^6$ and $R^7$ are each independently H, $C_{1-6}$alkyl or aryl.

In another embodiment, the compound of Formula XV(a) is a

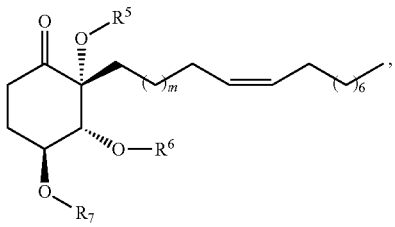

XV(a)(ii)

wherein m is 5, 7 or 9; and $R^5$, $R^6$ and $R^7$ are each independently H, $C_{1-6}$alkyl or aryl.

In an embodiment, the compound of Formula XV is a compound of Formula XV(b):

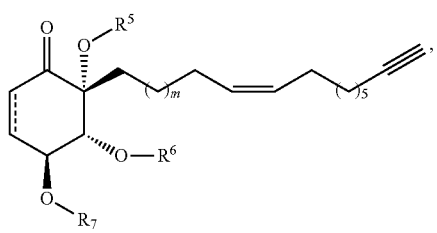

XV(b)

wherein

===== represents either a single bond or a double bond;

m is 5, 7 or 9; and $R^5$, $R^6$ and $R^7$ are each independently H, $C_{1-6}$alkyl or aryl.

In an embodiment, the compound of Formula XV(b) is a compound of Formula XV(b)(i):

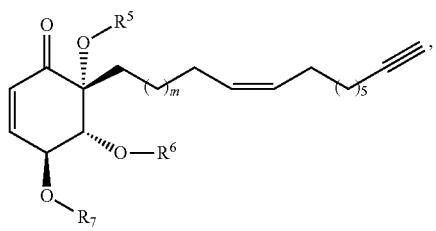

XV(b)(i)

wherein m is 5, 7 or 9; and $R^5$, $R^6$ and $R^7$ are each independently H, $C_{1-6}$alkyl or aryl.

In another embodiment, the compound of Formula XV(b) is a compound of Formula XV(b)(ii):

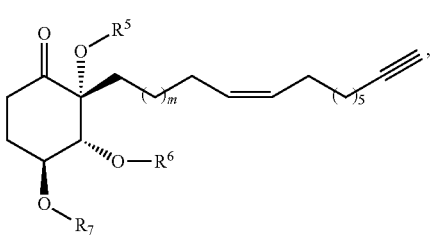

XV(b)(ii)

wherein m is 5, 7 or 9; and $R^5$, $R^6$ and $R^7$ are each independently H, $C_{1-6}$alkyl or aryl.

In an embodiment, m is 5. In another embodiment, m is 7. In a further embodiment, m is 9.

In an embodiment, $R^5$, $R^6$ and $R^7$ are each independently H, $C_{1-6}$alkyl or phenyl. In another embodiment, $R^5$, $R^6$ and $R^7$ are each independently H or $C_{1-6}$alkyl. In a further embodiment, $R^5$, $R^6$ and $R^7$ are all H.

In another embodiment of the present application, the compound of Formula XV(a)(i) is a compound of the following structure:

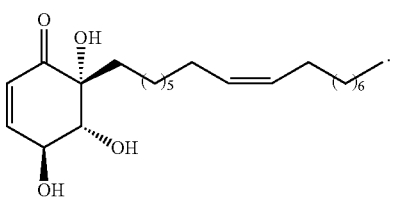

In another embodiment of the present application, the compound of Formula XV(a)(ii) is a compound of the following structure:

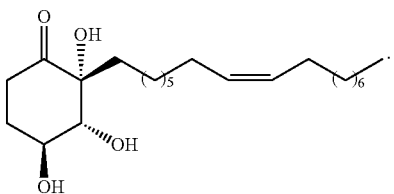

In another embodiment of the present application, the compound of Formula XV(b)(i) is a compound of the following structure:

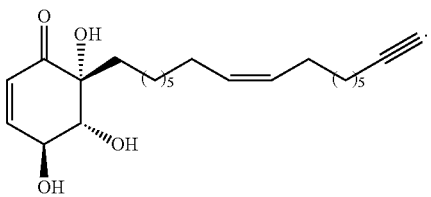

In another embodiment of the present application, the compound of Formula XV(b)(ii) is a compound of the following structure:

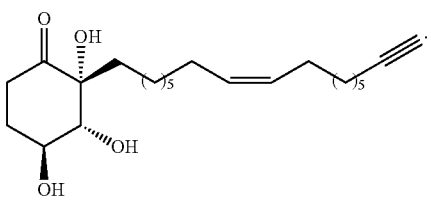

The conditions to react the compound of Formula XV(i) or Formula XV(ii) wherein $R^5$, $R^6$ and $R^7$ are all H under conditions to convert one or more of $R^5$, $R^6$ and $R^7$ to $C_{1-6}$alkyl or aryl are any suitable conditions. The selection of suitable conditions can be made by a person skilled in the art.

A person skilled in the art will appreciate that further derivatizations/modifications of the compounds of Formula XV(a) and Formula XV(b) are possible. For example, in some embodiments, when $R^5$, $R^6$ and/or $R^7$ are H, the hydroxyl groups are alkylated, arylated, acylated, oxidized, reduced and/or inverted using reagents and methods known in the art. In some embodiments, the ketone group is reduced or reacted with amines to form an imine. In some embodiments, the double bonds are reduced or oxidized.

Throughout the processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

III. Compounds

In some embodiments, processes of the present application are useful, for example, to prepare new alkynyl derivatives of pleiogenone A and other polyhydroxylated cyclohexenones.

Accordingly, the present application also includes a compound of Formula XV:

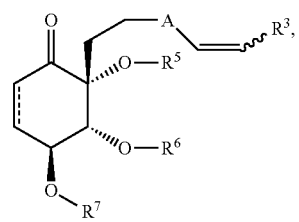

XV wherein

====== represents either a single bond or a double bond;
$R^3$ is $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl; and $R^5$, $R^6$ and $R^7$ are each independently H, $C_{1-6}$alkyl or aryl; and wherein one or more available hydrogens in $R^3$, $R^5$, $R^6$ and/or $R^7$ is/are optionally replaced with F and/or one or more of available atoms in $R^3$, $R^5$, $R^6$ and/or $R^7$ is/are optionally replaced with an isotopic label.

In an embodiment, $R^3$ is $C_{2-20}$alkynyl, wherein the alkynyl moiety is a terminal alkynyl moiety.

In an embodiment, the compound of Formula XV is a compound of Formula XV(b):

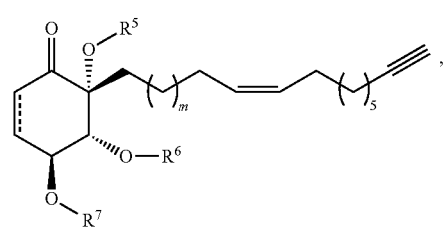

XV(b)

wherein

====== represents either a single bond or a double bond;
m is 5, 7 or 9; and
$R^5$, $R^6$ and $R^7$ are each independently H, $C_{1-6}$alkyl or aryl.

In an embodiment, the compound of Formula XV(b) is a compound of Formula XV(b)(i):

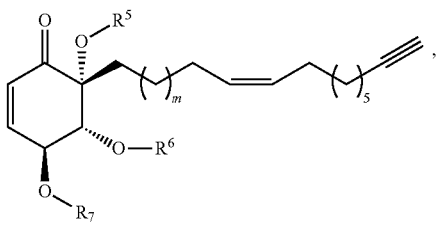

XV(b)(i)

wherein
m is 5, 7 or 9; and
$R^5$, $R^6$ and $R^7$ are each independently H, $C_{1-6}$alkyl or aryl.

In another embodiment, the compound of Formula XV(b) is a compound of Formula XV(b)(ii):

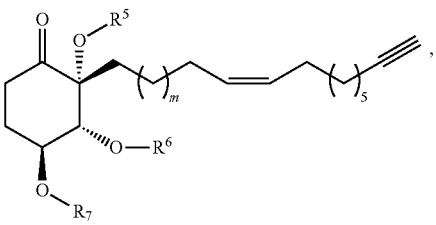

XV(b)(ii)

wherein
m is 5, 7 or 9; and
$R^5$, $R^6$ and $R^7$ are each independently H, $C_{1-6}$alkyl or aryl.

In an embodiment, m is 5. In another embodiment, m is 7. In a further embodiment, m is 9.

In an embodiment, $R^5$, $R^6$ and $R^7$ are each independently H, $C_{1-6}$alkyl or phenyl. In another embodiment, $R^5$, $R^6$ and $R^7$ are each independently H or $C_{1-6}$alkyl. In a further embodiment, $R^5$, $R^6$ and $R^7$ are all H.

In another embodiment of the present application, the compound of Formula XV(b)(i) is a compound of the following structure:

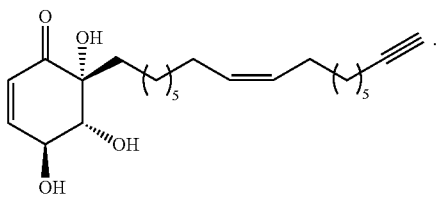

In another embodiment of the present application, the compound of Formula XV(b)(ii) is a compound of the following structure:

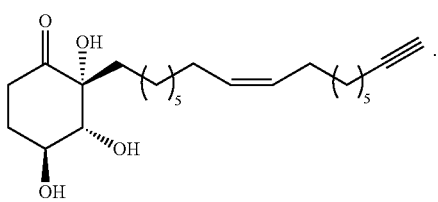

The following non-limiting examples are illustrative of the present application:

EXAMPLES

Example 1

Chemoenzymatic Synthesis of antiproliferative trihydroxyalkylcyclohexenone isolated from *Pleiogynium timorense*

I. Experimental Procedures

Experimental procedures and are provided for representative compounds.

(a) Preparation of (3aS,7aR)-methyl 2,2-dimethyl-3a,7a-dihydrobenzo[d][1,3]dioxole-3a-carboxylate (11)[2,3,4,5]

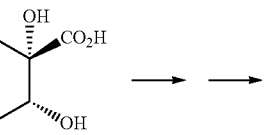

6

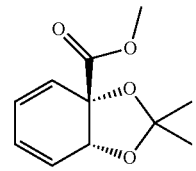

11

To 75 mL of a 40% aqueous solution of KOH was added 250 mL of diethyl ether, and the stirring solution was cooled to 0° C. To the stirring solution was added nitrosomethylurea (25 g, 243 mmol) in portions over 5 minutes. The deep yellow ether layer was then decanted into a solution of acid 6 (7.6 g, 49 mmol) in THF (125 mL) at 0° C. The reaction mixture was allowed to warm to room temperature with continuous stirring, and the reaction progress was monitored by TLC. After 4 h the reaction was deemed to be complete, and the ethereal solvents were removed under reduced pressure. The crude mixture was then dissolved in 2,2-dimethoxy propane (2,2-DMP; 50 mL) and stirred at room temperature. To the stirring mixture was added a catalytic amount of p-TsOH, and the reaction progress was monitored by TLC. After 4 h the reaction was deemed to be complete, and the 2,2-DMP was evaporated under reduced pressure. The crude reaction mixture was purified by flash column chromatography [Hexanes:EtOAc (4:1)] to afford ester 11 as a clear colourless oil which solidified to a white crystalline solid upon standing (7.4 g, 35 mmol, 70%).

11: $R_f$=0.67 [2:1 (petrol:Et$_2$O)]; mp 48-51° C. (EtOAc: pentane) [lit.[4,5] mp 49-51° C.]; $[\alpha]_D^{20}$=−397.3 (c=1.0, CHCl$_3$) [lit.[4,5] $[\alpha]_D^{20}$=−417.2 (c=1.0, CHCl$_3$)]; IR (film) ν 3041, 2977, 2956, 2924, 1750, 1735, 1453, 1432, 1384, 1368, 1251, 1214, 1166, 1081, 1044, 885, 805, 710; $^1$H NMR (300 MHz, CDCl$_3$) δ 6.10-6.00 (m, 2H), 6.00-5.92 (m, 1H), 5.80-5.73 (m, 1H), 4.90 (d, J=4.1 Hz, 1H), 3.72, (s, 3H), 1.37 (s, 3H), 1.35 (s, 3H); $^{13}$C NMR (75 MHz, CDCl$_3$) δ 172.1, 124.7, 124.5, 124.1, 124.0, 106.8, 79.4, 72.7, 52.9, 26.9, 25.2.

(b) Preparation of ((3aR,7aR)-2,2-dimethyl-3a,7a-dihydrobenzo[d][1,3]dioxol-3a-yl)methanol (12)[2], 4,5

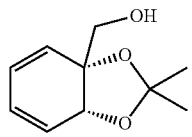

Ester 11 (9.8 g, 46.6 mmol) was dissolved in THF (400 mL) and the stirring solution was cooled to 0° C. To the stirring mixture was added a solution of LiBH$_4$ (1.93 g, 88.5 mmol, 2.0 M in THF) dropwise over 5 min. The solution was stirred at 0° C. for 1 h before being allowed to warm to room temperature with continuous stirring for 4 h. The reaction mixture was then quenched with dropwise addition of EtOAc (200 mL) followed by H$_2$O (300 mL). The resulting solution was extracted with EtOAc (3×300 mL) and the combined organic extracts were dried over MgSO$_4$. The crude extract was concentrated under reduced pressure and purified by flash column chromatography [Hexanes:EtOAc (4:1)] to afford alcohol 12 as a clear, colourless oil which solidified to a white crystalline solid upon standing (7.3 g, 40.1 mmol, 86%).

12: mp 42-44° C. (EtOAc:pentane) [lit.[4,5] mp 42-43° C.]; $[\alpha]_D^{20}$=-211.4 (c=0.8, CHCl$_3$) [lit.[4,5] $[\alpha]_D^{20}$=-215.9 (c=1.0, CHCl$_3$)]; IR (nujol) v 3392, 1643, 1594; $^1$H NMR (300 MHz, CDCl$_3$) δ6.08 (dd, J=9.9, 5.0 Hz, 1H), 5.99 (d, J=9.9 Hz, 1H), 5.98 (d, J=9.9 Hz, 1H), 5.67 (d, J=9.9 Hz, 1H), 4.47 (d, J=5.0 Hz, 1H), 3.56 (d, J=11.5 Hz, 1H), 3.34 (d, J=11.5 Hz, 1H), 2.25 (s, 1H), 1.43 (s, 3H), 1.35 (s, 3H); $^{13}$C NMR (75 MHz, CDCl$_3$) δ 128.9, 125.1, 124.4, 123.4, 106.3, 80.5, 70.9, 64.3, 27.1, 26.6.

(c) Preparation of (3aS,7aR)-3a-((Z)-8,8-dimethoxyoct-1-en-1-yl)-2,2-dimethyl-3a,7a-dihydrobenzo[d][1,3]dioxole (17)

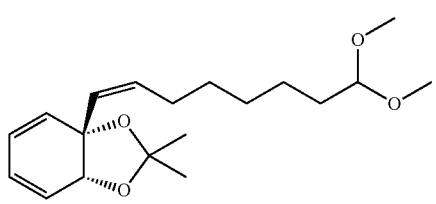 [SMILES: COC(CCCCC/C=C\[C@]12C=CC=C[C@H]1OC(C)(C)O2)OC]

To a stirred solution of DMSO (117 μL, 1.50 mmol), in CH$_2$Cl$_2$ (20 mL) at −78° C. was added oxalyl chloride (64 μL, 0.75 mmol), and the solution was allowed to stir for 15 min. To the stirring solution was added alcohol 12 (0.09 g, 0.50 mmol) in CH$_2$Cl$_2$ (10 mL) dropwise over 5 min, and the solution was allowed to stir for 1 h. To the stirring solution was then added triethylamine (279 μL, 2.0 mmol) at −78° C., and the solution was allowed to stir for 1 h before being warmed to room temperature over 12 h. The reaction mixture was then poured into water (15 mL), and the aqueous solution extracted with CH$_2$Cl$_2$ (3×15 mL). The combined organic layers were washed with brine (1×5 mL), dried over MgSO$_4$ and the solvent removed under reduced pressure. The crude residue was passed through a short pad of silica to afford aldehyde 15 as a pale yellow oil, which was used immediately without further purification. To a stirring solution of phosphonium bromide 16 (0.25 g, 0.60 mmol) in THF (2 mL) at −78° C. was added n-BuLi (0.3 mL, 2.38 M) dropwise over 2 min. The reaction mixture was stirred at −78° C. for 15 min before being allowed to warm to room temperature. The reaction mixture was then cooled to −78° C. before the dropwise addition of aldehyde 15 (0.09 g, 0.50 mmol) over 5 min. The reaction mixture was stirred at −78° C. for 3 h before being allowed to warm to room temperature. The reaction was then quenched with a saturated aqueous solution of NH$_4$Cl (2 mL) and the product extracted with EtOAc (3×2 mL). The combined organic extracts were dried over Na$_2$SO$_4$, and concentrated under reduced pressure. The crude reaction mixture was purified by flash column chromatography [15:1, Hex:EtOAc] to afford olefin 17 (0.03 mg, 0.09 mmol, 20%) as a clear, colourless oil.

17: R$_f$=0.57 [4:1 (Hexanes:EtOAc)]; $[\alpha]_D^{20}$=-195.1 (c=1.9, CHCl$_3$); IR (film) v 2933, 2858, 1456, 1379, 1260, 1210, 1127, 1030, 890, 800, 710; $^1$H NMR (300 MHz, CDCl$_3$) δ6.11 (dd, J=9.9, 5.5, 1H), 6.01 (dd, J=9.8, 4.5, 1H), 5.86 (ddd, J=9.5, 5.4, 0.9, 1 H), 5.76 (d, J=9.5, 1H), 5.58 (dt, J=11.6, 1.4, 1 H), 5.45-5.36 (m, 1H), 4.39 (d, J=4.3, 1H), 4.33 (t, J=5.7, 1H), 3.30 (s, 6H), 2.06-1.99 (m, 2H), 1.60-1.53 (m, 2H), 1.41 (s, 3H), 1.37 (s, 3H), 1.34-1.24 (m, 6H); $^{13}$C NMR (75 MHz, CDCl$_3$) δ 133.3, 133.0, 130.3, 125.1, 124.0, 104.8, 104.5, 79.5, 76.2, 52.6, 32.4, 29.5, 29.2, 28.5, 27.0, 25.8, 24.5; MS (EI) m/z 338 (20), 322 (32), 321 (100), 264 (30), 255 (39), 232 (98), 201 (90), 200 (67), 173 (35), 172 (29), 171 (26), 159 (26), 157 (44), 145 (47), 133 (49), 123 (28), 107 (47), 105 (21), 75 (20); HRMS (EI) 322.2144=C$_{19}$H$_{30}$O$_4$; calcd C$_{19}$H$_{20}$O$_4$[(M−1)$^+$, H]: 321.2066. Found: 321.2079; Anal. calcd. for C$_{19}$H$_{30}$O$_4$: C, 70.77, H, 9.38; found: C, 70.89, H, 9.57.

(d) Preparation of (3aS,4R,7S,7aR)-3a-((Z)-8,8-dimethoxyoct-1-en-1-yl)-2,2-dimethyl-3a,4,7,7a-tetrahydro-4,7-epidioxybenzo[d][1,3]dioxole (18)

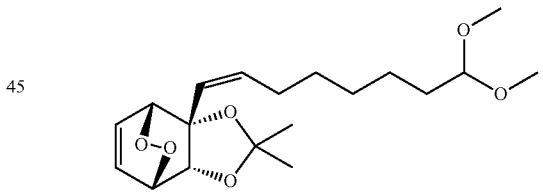

Olefin 17 (0.25 g, 0.78 mmol) was dissolved in CH$_2$Cl$_2$ (200 mL) in a water-jacketed flask, and tetraphenylporphyrin (0.02 g, 0.04 mmol) was added to the stirring mixture. The stirring solution was irradiated in a water cooled reaction vessel using a 500 W lamp while O$_2$ was bubbled through continuously. The reaction was monitored using $^1$H NMR, and the reaction was deemed to be complete after 40 h. The solvent was evaporated under reduced pressure and the crude mixture was purified by column chromatography [toluene to hexanes-EtOAc (9:1)] to afford endoperoxide 18 as a clear colourless oil (0.20 g, 0.56 mmol, 72%).

18: R$_f$=0.32 [4:1 (Hexanes:EtOAc)]; $[\alpha]_D^{20}$=-12.4 (c=1.4, CHCl$_3$); $^1$H NMR (300 MHz, CDCl$_3$) δ 6.65 (td, J=6.2, 1.6, 1H), 6.50 (td, J=6.2, 1.5, 1H), 5.73-5.57 (m, 2H), 4.66 (dt, J=6.1, 1.6, 1H), 4.37-4.33 (m, 2H), 3.31 (s, 6H), 2.43-2.26 (m, 2H), 1.63-1.57 (m, 2H), 1.43-1.33 (m, 6H), 1.31 (s, 6H); $^{13}$C NMR (75 MHz, CDCl$_3$) δ 135.4, 132.4, 132.0, 129.4, 110.9, 104.5, 79.7, 78.0, 77.8, 72.6, 52.6, 32.4, 29.5, 29.2, 28.7, 26.9, 26.2, 24.5.

(e) Preparation of (3aS,4R,7S,7aR)-3a-((Z)-8,8-dimethoxyoct-1-en-1-yl)-2,2-dimethyl-3a,4,7,7a-tetrahydrobenzo[d][1,3]dioxole-4,7-diol (19)

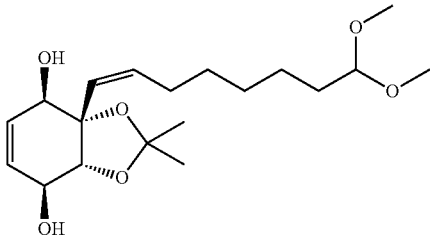 [SMILES: COC(CCCCC/C=C\[C@@]12OC(C)(C)O[C@@H]1[C@@H](O)C=C[C@H]2O)OC]

A solution of thiourea (5 mg, 0.06 mmol) in methanol (0.5 mL) was added dropwise over 20 min to a stirred solution of endoperoxide 18 (20 mg, 0.05 mmol) in $CH_2Cl_2$ (1 mL) at room temperature. The resulting suspension was stirred at room temperature for 1.5 h before being filtered and concentrated under reduced pressure. The crude product was purified by flash column chromatography [Hexanes-EtOAc (4:1)] to afford diol 19 as a clear colourless oil (15 mg, 0.04 mmol, 74%).

19: $R_f$=0.41 [1:1 (Hexanes:EtOAc)]; $[\alpha]_D^{20}$=+8.7 (c=0.9, $CHCl_3$); IR (film) v 3433, 2987, 2933, 2856, 1455, 1380, 1259, 1212, 1127, 1056, 885, 789, 718; $^1$H NMR (300 MHz, $CDCl_3$) δ6.09-6.00 (m, 2H), 5.72-5.63 (m, 1H), 5.44 (dt, J=11.7, 1.5, 1H), 4.36 (t, J=5.8, 1H), 4.31-4.28 (m, 2H), 4.18 (dd, J=5.5, 3.3, 1H), 3.31 (s, 6H), 2.46-2.38 (m, 2H), 1.63-1.58 (m, 2H), 1.40-1.36 (m, 12H); $^{13}$C NMR (75 MHz, $CDCl_3$) δ 136.3, 132.4, 131.5, 129.2, 109.4, 104.5, 85.6, 85.2, 71.2, 68.4, 52.7, 52.6, 32.4, 29.6, 29.2, 28.6, 27.5, 25.9, 24.2; MS (EI) m/z 341 (17), 324 (16), 294 (14), 293 (100), 270 (88), 239 (52), 238 (98), 235 (36), 181 (35), 149 (43), 148 (28), 125 (25), 120 (39), 107 (30), 99 (20), 75 (67); HRMS (EI) 356.2199=$C_{19}H_{32}O_6$; calcd $C_{19}H_{32}O_6$[(M-15)$^+$, $CH_3$]: 341.1985. Found: 341.1964.

(f) Preparation of (3aS,4R,7S,7aR)-3a-((Z)-8,8-dimethoxyoct-1-en-1-yl)-2,2-dimethyl-7-((triisopropylsilyl)oxy)-3a,4,7,7a-tetrahydrobenzo[d][1,3]dioxol-4-ol (20)

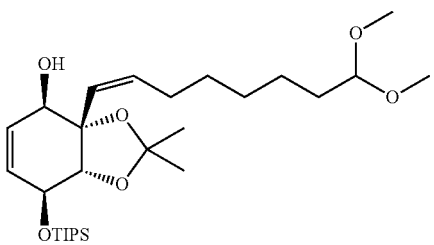

To a stirring solution of diol 19 (0.35 mg, 0.98 mmol) and 2,6-lutidine (0.25 mL, 2.16 mmol) in $CH_2Cl_2$ (15 mL) at −78° C. was added triisopropylsilane triflate (0.29 mL, 1.08 mmol) dropwise over 5 min. The reaction mixture was slowly warmed up to room temperature over 3 hours. A saturated aqueous solution of $NH_4Cl$ (20 mL) was added and the aqueous layer extracted with $CH_2Cl_2$ (3×20 mL). The combined organic extracts were dried with $Mg_2SO_4$, filtered and concentrated under reduced pressure. The crude mixture was purified by flash column chromatography [4:1 (Hexanes: EtOAc)] to afford the silyl ether 20 (0.33 mg, 0.64 mmol, 63%) as a clear colourless oil.

20: $R_f$=0.37 [4:1 (Hexanes:EtOAc)]; $[\alpha]_D^{20}$=+25.4 (c=1.0, $CHCl_3$); IR (film) v 3469, 2942, 2866, 1463, 1380, 1258, 1212, 1125, 1060, 883, 683; $^1$H NMR (300 MHz, $CDCl_3$) δ5.79-5.70 (m, 2H), 5.52 (dt, J=12.0, 7.5, 1 H), 5.31 (dt, J=12.0, 1.5, 1H), 4.47-4.45 (m, 1H), 4.37 (t, J=5.7, 1H), 4.15 (d, J=2.7, 1H), 4.14-4.12 (m, 1H), 3.32 (s, 6H), 2.41 (m, 2H), 1.62-1.56 (m, 2H), 1.47 (s, 3H), 1.41 (s, 3H), 1.40-1.37 (m, 6H), 1.16-1.10 (m, 22H); $^{13}$C NMR (75 MHz, $CDCl_3$) δ 134.4, 133.9, 130.8, 129.8, 108.9, 104.5, 85.6, 85.3, 70.7, 68.4, 52.6, 52.5, 32.4, 29.8, 29.3, 28.6, 27.5, 26.0, 24.6, 17.9, 12.0; MS (EI) m/z 462 (24), 450 (21), 449 (86), 448 (79), 438 (20), 437 (100), 405 (15), 404 (14), 391 (28), 390 (19), 380 (16), 379 (62), 373 (15), 372 (21), 362 (14), 361 (43), 345 (20); HRMS (EI) 512.3533=$C_{28}H_{22}O_6Si$; calcd $C_{27}H_{48}O_5Si$ [(M−32)$^+$, $CH_3OH$]: 480.3271. Found: 480.4282.

(g) Preparation of (3aR,7S,7aR)-3a-((Z)-8,8-dimethoxyoct-1-en-1-yl)-2,2-dimethyl-7-((triisopropylsilyl)oxy)-7,7a-dihydrobenzo[d][1,3]dioxol-4(3aH)-one (22)

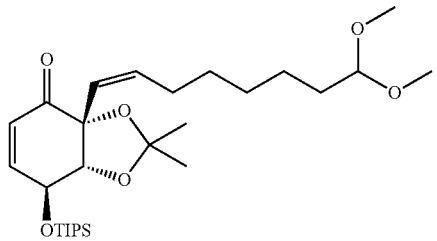

Silyl ether 20 (215 mg, 0.42 mmol) was dissolved in ethyl acetate (20 mL) and 2-iodoxybenzoic acid (IBX; 123 mg, 0.46 mmol) was added in portions. The reaction mixture was heated to reflux and monitored by TLC and the reaction was observed to be complete after 4 h. The crude suspension was filtered, washed with a saturated aqueous solution of $NaHCO_3$ (1×5 mL), and the organic layer was concentrated under reduced pressure. The crude reaction mixture was purified by flash column chromatography [4:1 (Hexanes: EtOAc)] to afford enone 22 (196 mg, 0.38 mmol, 91%) as a pale yellow oil.

22: $R_f$=0.43 [4:1 (Hexanes:EtOAc)]; $[\alpha]_D^{20}$=−69.5 (c=1.6, $CHCl_3$); IR (film) v 2942, 2867, 1698, 1463, 1383, 1229, 1127, 1077, 1053, 882, 844, 790, 684; $^1$H NMR (300 MHz, $CDCl_3$) δ6.74 (ddd, J=10.2, 4.5, 1.8, 1H), 6.06 (d, J=10.2, 1H), 5.59 (dt, J=11.6, 7.4, 1H), 5.44 (d, J=11.7, 1H), 4.70 (d, J=4.5, 1.0, 1H), 4.34 (t, J=5.7, 1H), 4.25 (t, J=5.7, 1H), 3.30 (s, 6H), 2.55-2.39 (m, 1H), 2.39-2.22 (m, 1H), 1.63-1.51 (m, 2H), 1.44-1.26 (m, 12H), 1.25-0.99 (m, 22H); $^{13}$C NMR (75 MHz, $CDCl_3$) δ 196.8, 144.4, 137.3, 127.7, 122.7, 109.3, 104.6, 83.3, 83.0, 65.4, 52.6, 32.5, 29.5, 29.1, 28.7, 27.4, 26.5, 24.6, 17.9, 12.2; MS (EI) m/z 510 (20), 502 (97), 479 (68), 429 (63), 421 (38), 414 (100), 403 (47), 223 (69), 205 (41), 174 (66), 162 (92), 146 (98), 131 (82), 103 (74), 91 (50); HRMS (EI) $C_{28}H_{20}O_6Si$ calcd: 510.3377. Found: 510.3362.

(h.1) Preparation of (3aR,7S,7aR)-3a-((Z)-heptadec-8-en-1-yl)-2,2-dimethyl-7-((triisopropylsilyl)oxy)-7,7a-dihydrobenzo[d][1,3]dioxol-4(3aH)-one (27)

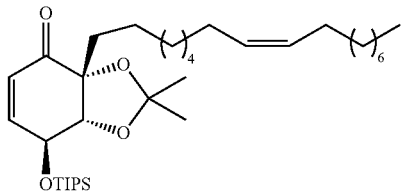

To a stirring solution of enone 22 (70 mg, 0.14 mmol) in CH$_2$Cl$_2$ (3 mL) was added thiophenol (15 μL, 0.15 mmol) and Et$_3$N (3 μL, 0.014 mmol). The solution was allowed to stir at room temperature, and the reaction monitored by TLC. After 12 h the reaction was deemed to be complete, and the reaction mixture concentrated under reduced pressure. The crude mixture was passed through a short pad of silica to afford the corresponding thioadduct [$^1$H NMR (300 MHz, CDCl$_3$) δ 7.47-7.43 (m, 2H), 7.35-7.29 (m, 3H), 5.65-5.59 (m, 2H), 4.47-4.42 (m, 1H), 4.35 (t, J=5.8, 1H), 4.18-4.16 (m, 1H), 3.63-3.59 (m, 1H), 3.31 (s, 6H), 3.21-3.14 (m, 1H), 2.47-2.38 (m, 2H), 2.22-2.16 (m, 1H), 1.70-1.48 (m, 2H), 1.39 (s, 3H), 1.35-1.29 (m, 9H), 0.99-0.86 (m, 14H), 0.20-0.12 (m, 7H)], which was then dissolved in MeOH (2 mL). To the methanolic solution was added Wilkinson's catalyst (130 mg, 0.14 mmol), and the reaction mixture was allowed to stir at room temperature under 1 atm of H$_2$. The reaction progress was monitored by TLC, and after 20 h the reaction was deemed to be complete. The crude mixture was filtered through a short pad of silica to afford thioether 23 [$^1$H NMR (300 MHz, CDCl$_3$) δ 7.46-7.42 (m, 2H), 7.35-7.27 (m, 3H), 4.71-4.67 (m, 1H), 4.33 (t, J=5.7, 1H), 4.24 (t, 1.9, 1H), 3.68-3.65 (m, 1H), 3.30 (s, 6H), 3.20 (dd, J=14.0, 4.7, 1 H), 2.51 (ddd, J=14.0, 2.0, 1.0, 1H), 1.93-1.84 (m, 1H), 1.80-1.69 (m, 1H), 1.60-1.53 (m, 2H), 1.38 (s, 3H), 1.29-1.16 (m, 13H), 1.14-1.07 (m, 21H)], which was then dissolved in CH$_2$Cl$_2$ (2 mL) and stirred at room temperature. To the stirring solution was added DBU (21 μL, 0.15 mmol), and the reaction progress was monitored by TLC. The reaction was deemed to be complete after 8 h. The crude reaction mixture was concentrated under reduced pressure and purified by flash column chromatography to afford enone 24 as a clear colourless oil (37 mg, 0.07 mmol, 53%) [$^1$H NMR (300 MHz, CDCl$_3$) δ 6.75 (ddd, J=10.2, 4.7, 2.0, 1H), 6.04 (d, J=10.2, 1H), 4.70 (dd, J=4.7, 1.5, 1H), 4.34 (t, J=5.6, 1H), 4.25 (t, J=1.5, 1H), 3.31 (s, 6H), 1.80-1.75 (m, 2H), 1.60-1.54 (m, 2H), 1.39 (s, 3H), 1.32-1.25 (m, 13H), 1.14-1.07 (m, 21H)]. Enone 24 (35 mg, 0.07 mmol) was dissolved in a prepared solution of iodine (1.7 mg, 0.007 mmol) in acetone (0.6 mL), stirred at room temperature, and the reaction progress was monitored by TLC. After 10 min the reaction was deemed to be complete, and the reaction mixture was diluted with CH$_2$Cl$_2$ (1 mL) and quenched with 5% aqueous solution of Na$_2$S$_2$O$_3$ (0.5 mL). The aqueous layer was separated and extracted with CH$_2$Cl$_2$ (3×0.5 mL). The combined organic extracts were washed with brine (1×0.3 mL), dried with Na$_2$SO$_4$ and the solvent was removed under reduced pressure to afford aldehyde 25 [$^1$H NMR (300 MHz, CDCl$_3$) δ9.75 (t, J=1.8, 1H), 6.76 (ddd, J=10.2, 4.7, 1.8, 1H), 6.05 (d, J=10.1, 1H), 4.71 (dd, J=4.6, 1.5, 1H), 4.24 (t, J=1.6, 1H), 2.40 (td, J=7.3, 1.7, 2H), 1.80-1.75 (m, 2H), 1.62-1.51 (m, 2H), 1.39 (s, 3H), 1.33-1.26 (m, 11H), 1.14-1.06 (m, 21H)], which was used immediately in the next step. To a stirring solution of phosphonium bromide 26 (35 mg, 0.08 mmol) in THF (1 mL) at −78° C. was added n-BuLi (38 μL, 2.11 M) dropwise. The reaction mixture was stirred for 15 min before warming to room temperature. The reaction mixture was then cooled to −78° C. before the dropwise addition of aldehyde 25 over 5 min. The reaction mixture was stirred at −78° C. for 3 h before being allowed to warm to room temperature. The reaction was then quenched with a saturated aqueous solution of NH$_4$Cl (1 mL) and the product extracted with EtOAc (3×1 mL). The combined organic extracts were dried over Na$_2$SO$_4$, and concentrated under reduced pressure. The crude reaction mixture was purified by flash column chromatography [15:1, Hex:EtOAc] to afford enone 27 (22 mg, 0.04 mmol, 57%) as a clear, colourless oil. 27: R$_f$=0.53 [9:1 (Hexanes:EtOAc)]; [α]$_D^{20}$=+36.0 (c=0.4, CHCl$_3$); IR (film) ν 2926, 2855, 1695, 1463, 1372, 1240, 1177, 1065, 882, 845, 683; $^1$H NMR (300 MHz, CDCl$_3$) δ6.75 (ddd, J=10.2, 4.7, 1.9, 1H), 6.04 (d, J=10.2, 1H), 5.38-5.28 (m, 2H), 4.71 (dd, J=4.8, 1.4, 1H), 4.25 (t, J=1.6, 1H), 2.03-1.97 (m, 4H), 1.83-1.73 (m, 2H), 1.39 (s, 3H), 1.32-1.21 (m, 24H), 1.18-1.07 (m, 22H), 0.88 (t, J=7.0, 3H); $^{13}$C NMR (75 MHz, CDCl$_3$) δ 200.0, 144.3, 129.9, 129.8, 127.5, 108.3, 82.5, 80.9, 65.5, 33.8, 31.9, 29.9, 29.8, 29.7, 29.5, 29.4, 29.3, 27.3, 27.2, 27.2, 26.5, 23.2, 22.7, 17.9, 14.1, 12.2.

(h.2) Preparation of Alkynyl Enone Derivative

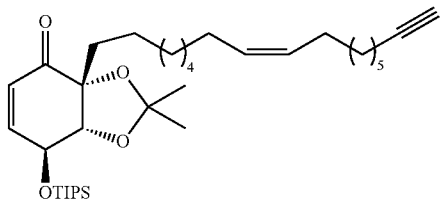

In a like manner, the alkynyl enone derivative is prepared. To a stirring solution of the phosphonium bromide

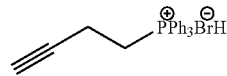

in THF (1 mL) at −78° C. is added n-BuLi dropwise. The reaction mixture is stirred for 15 min before warming to room temperature. The reaction mixture is then cooled to −78° C. before the dropwise addition of aldehyde 25 over 5 min. The reaction mixture is stirred at −78° C. for 3 h before being allowed to warm to room temperature. The reaction is then quenched with a saturated aqueous solution of NH$_4$Cl and the product extracted with EtOAc. The combined organic extracts are dried over Na$_2$SO$_4$, and concentrated under reduced pressure. The crude reaction mixture is purified by flash column chromatography to afford the alkynyl enone derivative.

(i.1) Preparation of Alkylcyclohexenone Natural Product (1)

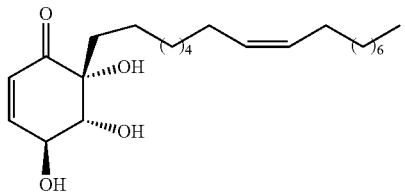

Enone 27 (5.0 mg, 0.009 mmol) was dissolved in a prepared solution of iodine (0.75 mg, 0.003 mmol) in acetonitrile (0.2 mL), and the solution was stirred at room temperature. The reaction progress was monitored by TLC, and the reaction was deemed to be complete after 10 h. The stirring mixture was diluted with $CH_2Cl_2$ (1 mL) and quenched with 5% aqueous solution of $Na_2S_2O_3$ (0.5 mL). The aqueous layer was separated and extracted with $CH_2Cl_2$ (3×0.5 mL), and the combined organic extracts were washed with brine (1×0.3 mL) and dried with $Na_2SO_4$. The solvent was removed under reduced pressure and the crude reaction mixture was purified by flash column chromatography [4:1 (Hexanes:EtOAc)] to afford natural product 1 (2.1 mg, 0.006 mmol, 64%) as a clear, colourless oil.

1: $[\alpha]_D^{20}$=+22.1 (c=0.2, $CHCl_3$) [lit.[6] $[\alpha]_D^{20}$=+23 (c=0.5, $CHCl_3$)]; $^1$H NMR (500 MHz, $CDCl_3$) δ 6.80 (ddd, J=10.1, 3.9, 1.4, 1H), 6.10 (dd, J=10.1, 0.8, 1H), 5.34 (m, 2H), 4.62 (brs, 1H), 3.98 (brs, 1H), 2.00 (m, 4H), 1.83 (m, 2H), 1.26 (m, 20H), 1.13 (m, 2H), 0.88 (t, J=6.9, 3H); $^{13}$C NMR (75 MHz, $CDCl_3$) 5200.2, 145.8, 129.9, 129.8, 126.4, 78.1, 75.4, 68.6, 38.9, 31.6, 29.8, 29.8, 29.7, 29.5, 29.3, 29.3, 29.2, 27.2, 27.2, 23.0, 22.7, 14.1; HRMS (ESI) 380.29=$C_{23}H_{40}O_4$; calcd $C_{23}H_{41}O_4[(M+1)^+H]$: 381.2999. Found: 381.2972.

(i.2) Preparation of Alkynyl Pleiogenone A

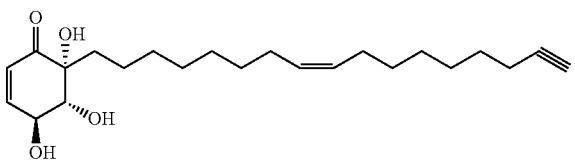 [SMILES: C#CCCCCCC/C=C\CCCCCCC[C@]1(O)C(=O)C=C[C@H](O)[C@H]1O]

In a like manner, the alkynyl pleiogenone A is prepared. The alkynyl enone derivative is dissolved in a prepared solution of iodine in acetonitrile, and the solution is stirred at room temperature. The reaction progress is monitored by TLC. The stirring mixture is diluted with $CH_2Cl_2$ and quenched with 5% aqueous solution of $Na_2S_2O_3$. The aqueous layer is separated and extracted with $CH_2Cl_2$, and the combined organic extracts are washed with brine and dried with $Na_2SO_4$. The solvent is removed under reduced pressure and the crude reaction mixture was purified by flash column chromatography to afford alkynyl pleiogenone A.

II. Results and Discussion

The common core of compounds 1-3 can be related to the ipso-diol 6 derived from benzoic acid by enzymatic dihydroxylation with *R. eutrophus* B9.[7] This diol serves as a convenient starting material for the synthesis of various natural products.[8] Enones 1-3 are not particularly complex structures yet they contain sensitive subunits and their synthesis presents a challenge in functional compatibility. The ipso-diol 6, containing a substructural unit of these enones with correct absolute stereochemistry is a useful starting material. It is obtained in multi-gram amounts by fermentation of benzoic acid with *R. eutrophus* B9 as previously described.[9] The initial plan for the synthesis of 1 was based on the endo-peroxide 7, prepared in five steps from the ipso-diol 6. The base-catalyzed Kornblum-DeLaMare rearrangement[10] of 7 provided the regioisomeric enone 8, as a consequence of the abstraction of the proton from the less hindered site, Scheme 2.

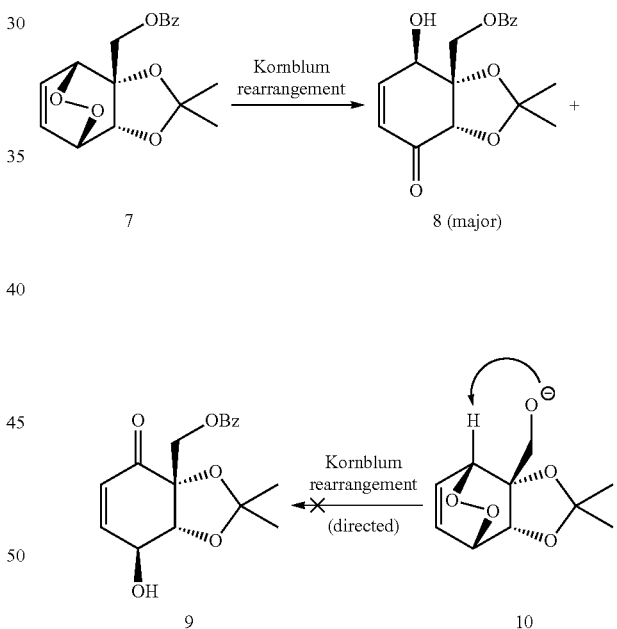

Attempts to solve the regiochemical issues by "directed" proton abstraction in 10 failed. Enones of the type 8 and 9 were obtained in essentially equal amounts from endoperoxides 7 and 10 and related compounds and their isolation from complex mixtures proved arduous.[11] Therefore the synthesis as shown in Scheme 3 was proceeded with. Esterification of the carboxylic acid in 6 and protection of the diol as its corresponding acetonide provided ester 11 whose reduction with $LiBH_4$ furnished alcohol 12.

Scheme 3

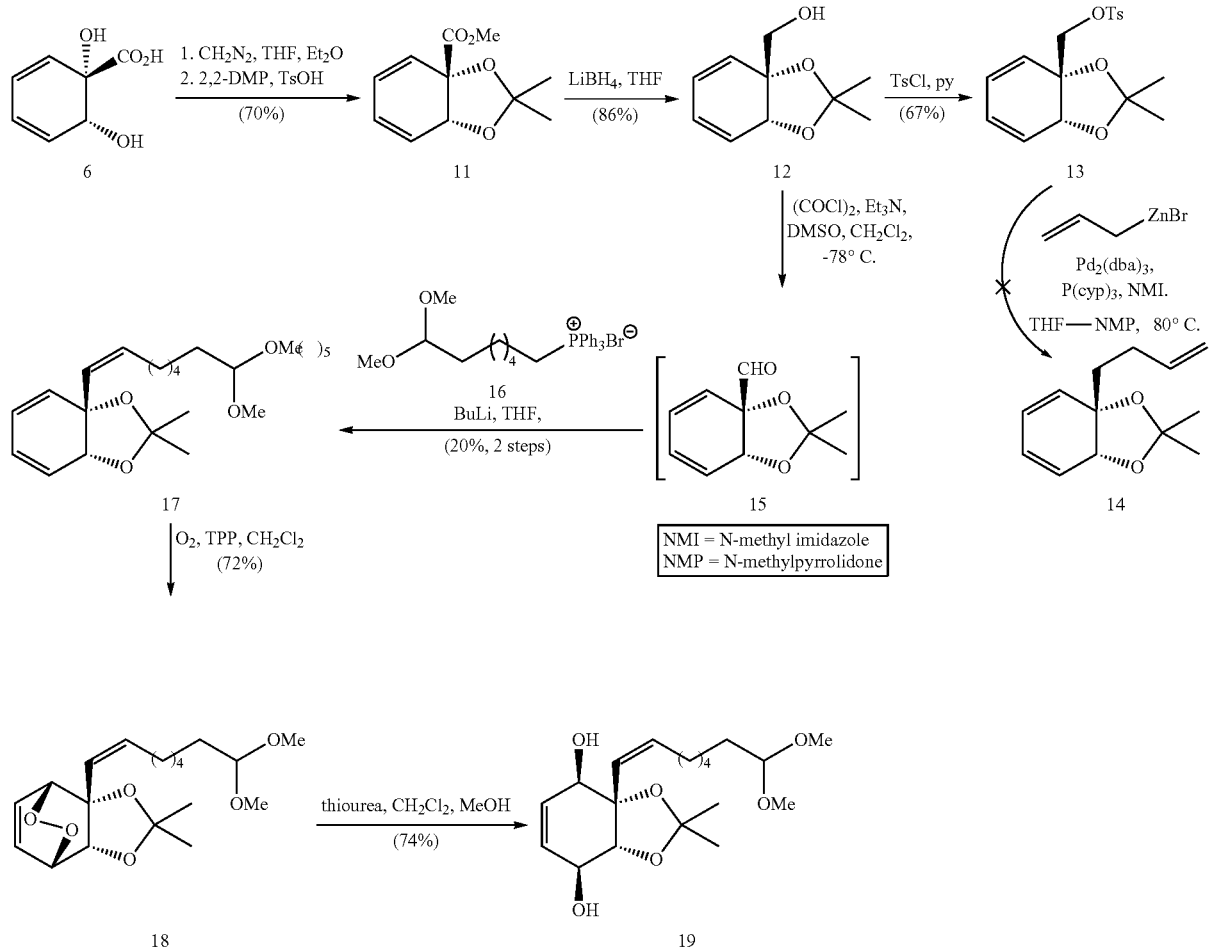

Alcohol 12 was first converted to tosylate 13 in anticipation of performing Negishi-type[12] coupling at this stage in order to introduce the side chain. However, model studies with allyl bromide proved unsuccessful, yielding only small amounts of the corresponding bromides with no allylation to 14 detected. In previous synthetic ventures with ipso-diol 6 it had been observed that the hydroxymethyl functionality is severely hindered and unresponsive in a variety of reactions.[13] Alcohol 12 was then converted to a rather labile aldehyde 15 and a Wittig reaction of the phosphonium salt 16 (synthesized from 1,7-heptanediol as has been reported for similar Wittig reagents)[14] furnished the triene 17 in 20% yield over the two steps, reflecting the instability of the aldehyde. An advantage of introducing the side chain in portions will ultimately allow for the synthesis of congeners 2 and 3 from the same intermediate.

The [2+4] cycloaddition of 17 with singlet oxygen produced the endo-peroxide 18 in good yields.[15] Although endo-peroxide 18 was initially isolated for full characterization, the cycloaddition and reduction steps in subsequent experiments were combined into a single operation without the need of isolation or purification.

As the Kornblum-DeLaMare rearrangement on the related endo-peroxide 7 did not proceed with required regiochemistry, this functionality was reduced completely with thiourea to diol 19 in anticipation that the steric hindrance inherent at the top portion of the molecule can be used in selective protection of the less hindered alcohol. Indeed, this proved to be the case and 19 was converted to enone 22 by first protecting the less hindered alcohol as its TIPS ether and subsequent oxidation with IBX in EtOAc, as shown in Scheme 4.

The protection was moderately selective furnishing the desired silyl ether 20 and its regioisomer 21 in a 3:1 ratio (21 is easily recycled by deprotection and resilylation). Several conditions were investigated for the selective hydrogenation of the side chain olefin but none of these proved successful. For example, in spite of many reported examples of the selective hydrogenation of olefins in the presence of an enone with Wilkinson's catalyst,[16] attempts to saturate the cis olefin in 22 and related model compounds failed.[13] Attempted saturation of the cis olefin 22 with potassium azodicarboxylate (PAD)[17] in nucleophilic solvents resulted in Michael-type addition to the enone and the use of non-nucleophilic solvents resulted in no reaction.[13]

Scheme 4

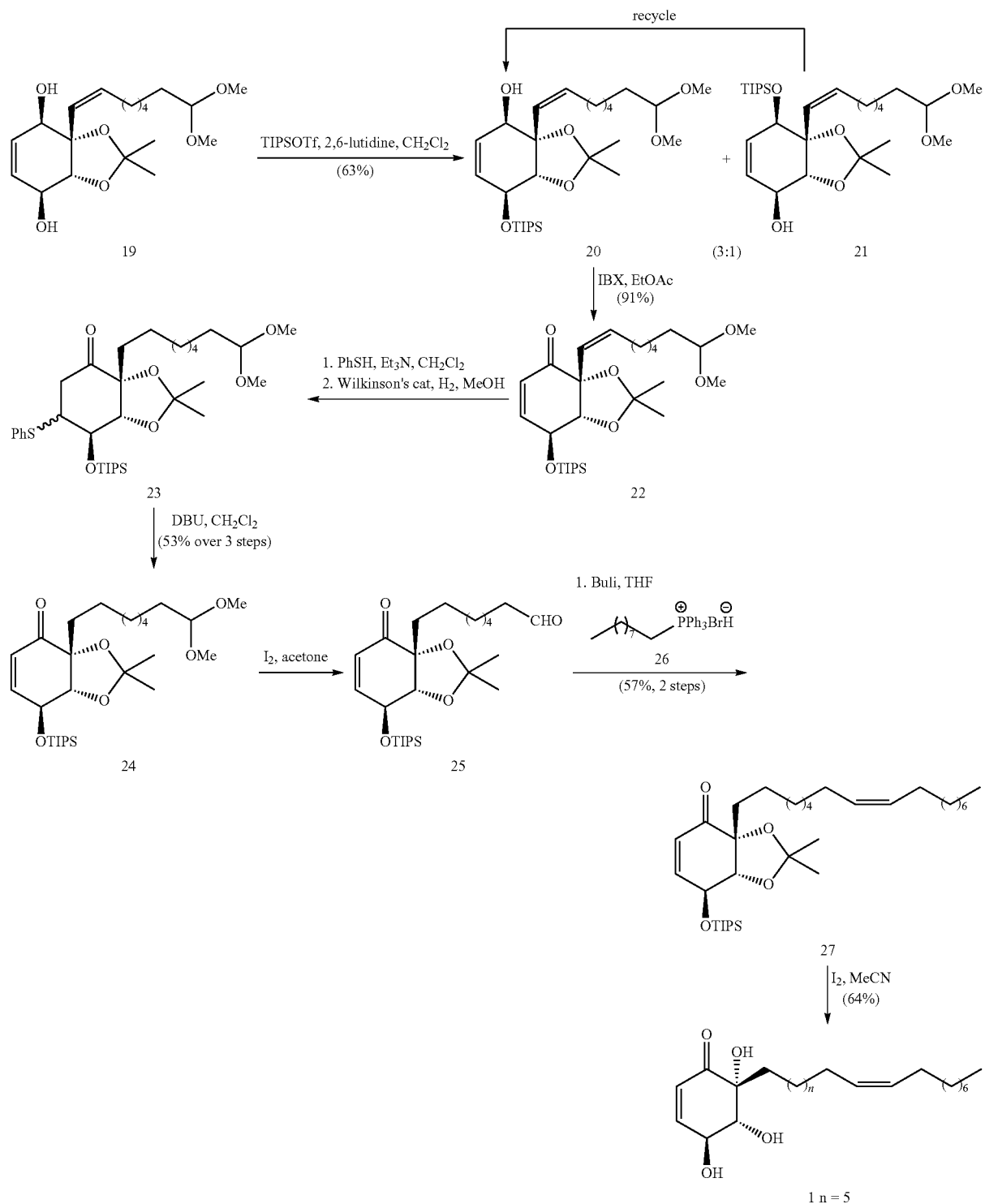

Enone 22 was therefore protected as its thiophenol adduct[18] whose hydrogenation in the presence of Wilkinson catalyst smoothly furnished 23 with the fully saturated side chain. Elimination of the thiophenyl ether was accomplished with DBU to provide enone 24 in 53% yield over three steps. The completion of the synthesis required selective hydrolysis of the acetal and this was accomplished with iodine in acetone.[19] The reaction of aldehyde 25 with the Wittig reagent derived from the phosphonium salt 26 (obtained from Alfa Aesar) led to 27, now containing the full side chain, in 57% yield over two steps.

Final deprotection of both the acetonide and the silyl ether was accomplished with iodine in acetonitrile[20] providing the desired enone 1 in 64% yield. The spectral and optical data matched those of the natural product.

In summary, the first chemoenzymatic enantioselective synthesis of hydroxylated enone 1 in 14 operations from benzoic acid is disclosed. The synthesis is modular allowing for the preparation of enones 2 and 3 from aldehyde 15 as a common intermediate. Variations in the rich functionalities contained in the cyclohexenone portion as well as changes in the side chain may, for example, be accomplished using the process described herein.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION

[1](a) A. L. Eaton, L. H. Rakotondraibe, P. J. Brodie, M. Goetz, D. G. I. Kingston, J. Nat. Prod. 2015, 78, 1752-1755; (b) A. L. Eaton, L. H. Rakotondraibe, P. J. Brodie, M. Goetz, D. G. I. Kingston, J. Nat. Prod. 2016, 79, DOI: 10.1021/asc.jnatprod.6b000373.

[2]G. N. Jenkins, D. W. Ribbons, D. A. Widdowson, A. M. Z. Slawin, D. J. Williams, J. Chem. Soc., Perkin Trans. 1 1995, 20, 2647-2656.

[3]A. G. Myers, D. R. Siegel, D. J. Buzard, M. G. Charest, Org. Lett. 2001, 3, 2923-2926.

[4]T. C. M. Fischer, H. G. Leisch, M. D. Mihovilovic, Monatsh. Chem. 2010, 141, 699-707.

[5]T. C. Fischer, B. Cerra, M. J. Fink, F. Rudroff, E. Horkel, M. D. Mihovilovic, Eur. J. Org. Chem. 2015, 7, 1464-1471.

[6]A. L. Eaton, L. H. Rakotondraibe, P. J. Brodie, M. Goetz, D. G. I. Kingston, J. Nat. Prod. 2015, 78, 1752-1755.

[7]A. M. Reiner, G. D. Hegeman, Biochemistry 1971, 10, 2530-2536.

[8]For a review see: S. E. Lewis, Chem. Commun. 2014, 50, 2821-2830.

[9]For detailed description of the fermentation procedure see: (a) Myers, A. G.; Siegel, D. R.; Buzard, D. J.; Charest, M. G., Org. Lett. 2001, 3, 2923-2926; For recent aplications of this diol in synthesis see: (b) D. R. Adams, C. Aichinger, J. Collins, U. Rinner, T. Hudlicky, Synlett 2011, 725-729; (c) M. J. Palframan, G. Kociok-Kohn, S. E. Lewis, Org. Lett. 2011, 13, 3150-3153; (d) J. A. Griffen, J. C. White, G. Kociok-Kohn, M. D. Lloyd, A. Wells, T. C. Arnot, S. E. Lewis, Tetrahedron 2013, 69, 5989-5997; (e) D. R. Adams, J. van Kempen, J. R. Hudlicky, T. Hudlicky, Heterocycles 2014, 88, 1255-1274.

[10](a) N. Kornblum, H. E. DeLaMare, J. Am. Chem. Soc. 1951, 73, 880-881; (b) Comprehensive Organic Name Reactions and Reagents (Ed.: Z. Wang), Wiley, Oxford, 2010, pp. 1675-1678; For mechanistic studies: (c) D. R. Kelly, H. Bansal, G. J. J. Morgan, Tetrahedron Lett. 2002, 43, 9331-9333. (d) E. Mete, R. Altundas, H. Secen, M. Balci, Turk. J. Chem. 2003, 27, 145-154; For Applications see: (e) H. Tan, X. Chen, Z. Liu, D. Z. Wang, Tetrahedron, 2012, 68, 3952-3955; (f) J. D. Parrish, M. A. Ischay, Z. Lu, S. Guo, N. R. Peters, T. P. Yoon, Org. Lett. 2012, 14, 1640-1643; (g) M. Zhang, N. Liu, W. Tang, J. Am. Chem. Soc. 2013, 135, 12434-12438; (h) X. Zheng, S. Lu, Z. Li, Org. Lett. 2013, 15, 5432-5435.

[11]D. R. Adams, PhD thesis, Brock University, 2014. Available from: http://hdl.handle.net/10464/5510.

[12](a) S. Baba, E. Negishi, J. Am. Chem. Soc. 1976, 98, 6729-6731; (b) J. Zhou, G. C. Fu, J. Am. Chem. Soc. 2003, 125, 12527-12530.

[13]See: D. R. Adams, J. van Kempen, J. R. Hudlicky, T. Hudlicky, Heterocycles 2014, 88, 1255-1274 for failed attempts to reduce the hydroxymethyl functionality to a methyl group.

[14](a) B. Hans Jurgen, S. Rainer, Synthesis 1989, 6, 419-422; (b) J.-H. Liu, Y. Jin, Y.-Q. Long, Tetrahedron 2010, 66, 1267-1273.

[15] For pioneering studies see: (a) M. Fritzsche, C. R. Acad. Sci. 1867, 64, 1035-1037; (b) A. Windaus, J. Brunken, Liebigs Ann. Chem. 1928, 460, 225-235; (c) C. Dufraisse, A. Etienne, C. R. Acad. Sci. 1935, 201, 280; (d) G. O. Schenck, Naturwissenschaften 1954, 32, 452-453; For reviews see: (e) E. L. Clennan, A. Pace, Tetrahedron, 2005, 61, 6665-6691; For applications see: (f) K. C. Nicolaou, S. Totokotsopoulos, D. Giguere, Y.-P. Sun, D. Sarlah, J. Am. Chem. Soc. 2011, 133, 8150-8153; (g) G. S. Buchanan, K. P. Cole, Y. Tang, R. P. Hsung, J. Org. Chem. 2011, 76, 7027-7039; (h) V. L. Paddock, R. J. Phipps, A. Conde-Angulo, A. Blanco-Martin, C. Giro-Manas, L. J. Martin, A. J. P. White, A. C. Spivey, J. Org. Chem., 2011, 76, 1483-1486.

[16]R. E. Ireland, P. Bey, Org. Synth. 1973, 53, 63-64.

[17]J. W. Hamersma, E. I. Snyder, J. Org. Chem. 1965, 30, 3985-3988.

[18](a) P. Wipf, S. R. Rector, H. Takahashi, J. Am. Chem. Soc. 2002, 124, 14848-14849; (b) C. J. Rosenker, E. H. Krenske, K. N. Houk, P. Wipf, Org. Lett. 2013, 15, 1076-1079.

[19]J. Sun, Y. Dong, L. Cao, X. Wang, S. Wang, Y. Hu, J. Org. Chem. 2004, 69, 8932-8934.

[20]J. S. Yadav, M. Satyanarayana, S. Raghavendra, E. Balanarsaiah, Tetrahedron Lett. 2005, 46, 8745-8748.

The invention claimed is:

1. A process for the preparation of a compound of Formula XV(i):

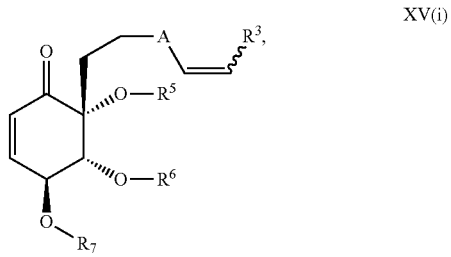

wherein

A is $C_{1-20}$alkylene;

$R^3$ is $C_{1-20}$alkyl, $C_{2-20}$alkenyl, $C_{2-20}$alkynyl, $C_{1-20}$alkylene-$R^4$, $C_{2-20}$alkenylene-$R^4$ or $C_{2-20}$alkynylene-$R^4$, wherein $R^4$ is $C_{3-10}$cycloalkyl, aryl or heteroaryl, and wherein the $C_{1-20}$alkyl, $C_{2-20}$alkenyl, $C_{2-20}$alkynyl, $C_{1-20}$alkylene, $C_{2-20}$alkenylene or $C_{2-20}$alkynylene is optionally substituted with one or more hydroxy groups; and $R^5$, $R^6$ and $R^7$ are each independently H, $C_{1-6}$alkyl or aryl, the process comprising:

(a) protecting a compound of Formula II under conditions to provide a compound of Formula III:

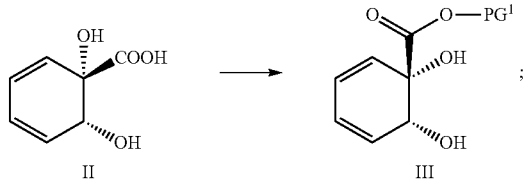

(b) protecting the compound of Formula III under conditions to provide a compound of Formula IV:

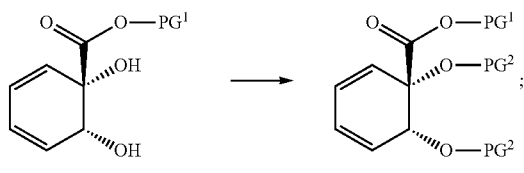

(c) reacting the compound of Formula IV with a first reducing agent under conditions to provide a compound of Formula V:

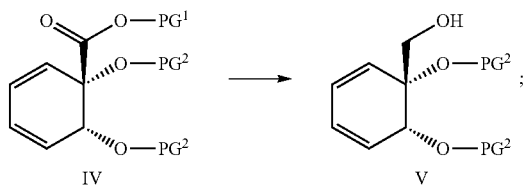

(d) reacting the compound of Formula V with a first oxidizing agent under conditions to provide a compound of Formula VI:

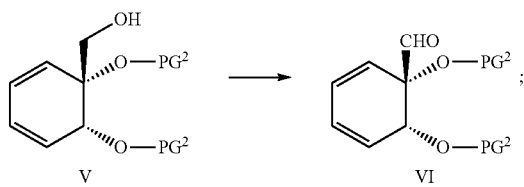

(e) reacting the compound of Formula VI with an alkene-forming reagent of Formula VII(a) under conditions to provide a compound of Formula VIII(a):

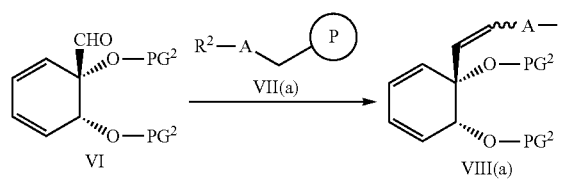

wherein the alkene-forming reagent is a Wittig reagent and

represents a triphenylphosphonium moiety or the alkene-forming reagent is a Horner-Wadsworth-Emmons reagent and

represents a phosphonate moiety; and $R^2$ is an acetal;

(f) reacting the compound of Formula VIII(a) with a source of singlet oxygen under conditions to provide an endoperoxide of formula IX(a):

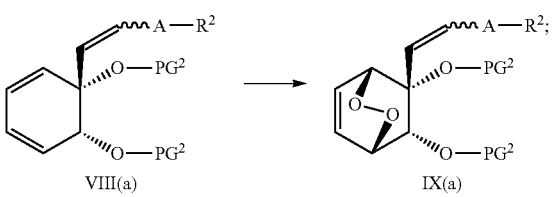

(g) reacting the endoperoxide of Formula IX(a) with a second reducing agent under conditions to provide a compound of Formula X(a):

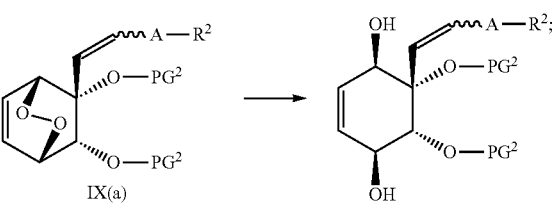

(h) protecting the compound of Formula X(a) under conditions to provide a compound of Formula XI(a)(i):

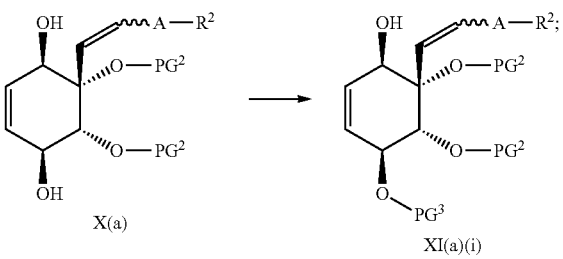

(i) reacting the compound of Formula XI(a)(i) with a second oxidizing agent under conditions to provide a compound of Formula I(a)(i):

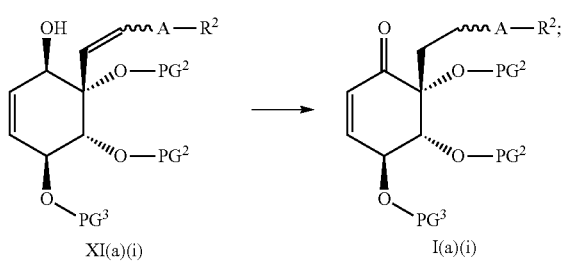

(j) protecting the compound of Formula I(a)(i) under conditions to provide a compound of Formula XIII(a):

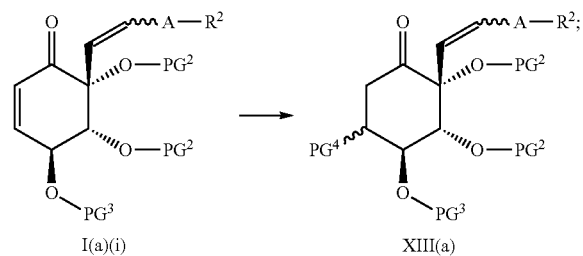

(k) hydrogenating the compound of Formula XIII(a) under conditions to provide a compound of Formula XIV(a):

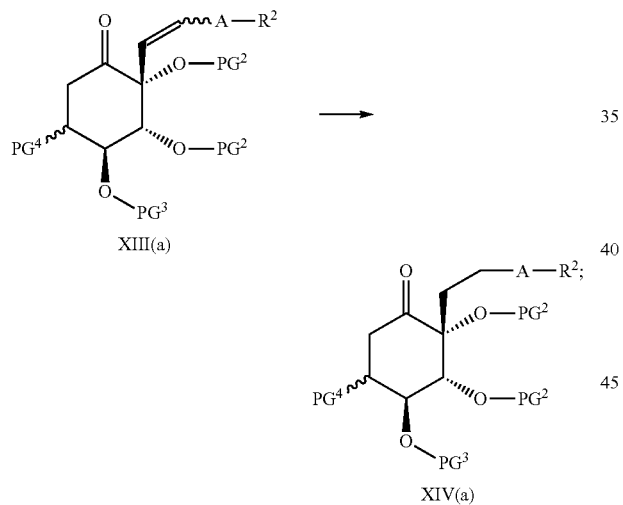

(l) deprotecting the compound of Formula XIV(a) under conditions to remove $PG^4$ and provide a compound of Formula XII(a):

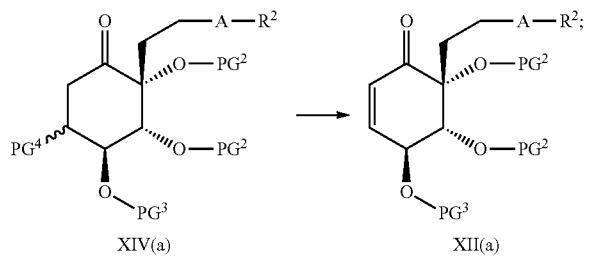

(m) reacting the compound of Formula XII(a) under conditions to convert $R^2$ into an aldehyde to provide a compound of Formula XVI(i):

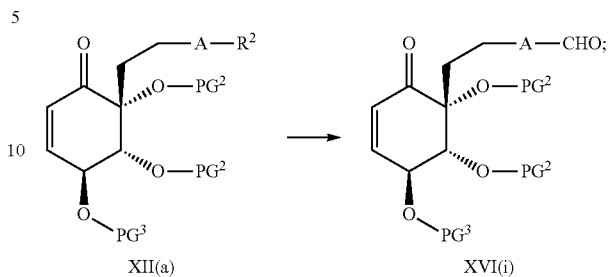

(n) reacting the compound of Formula XVI(i) with an alkene-forming reagent of Formula XVII under conditions to provide a compound of Formula XVIII(i):

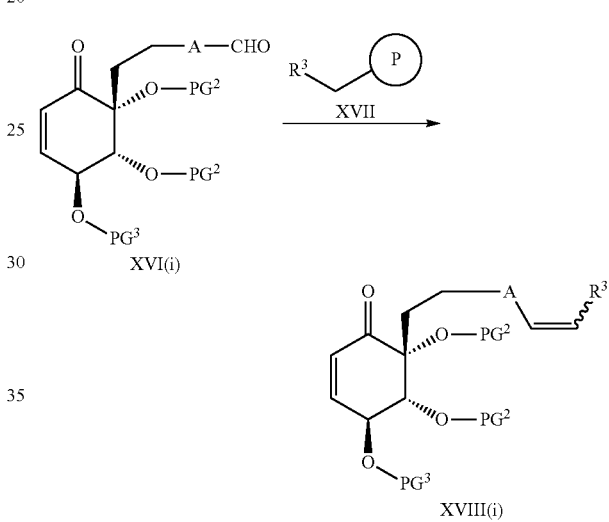

wherein
the alkene-forming reagent is a Wittig reagent and

represents a triphenylphosphonium moiety or the alkene-forming reagent is a Horner-Wadsworth-Emmons reagent and

represents a phosphonate moiety;

(o) deprotecting the compound of Formula XVIII(i) under conditions to provide the compound of Formula XV(i) wherein $R^5$, $R^6$ and $R^7$ are all H; and (p) optionally reacting the compound of Formula XV(i) wherein $R^5$, $R^6$ and $R^7$ are all H under conditions to convert one or more of $R^5$, $R^6$ and $R^7$ to $C_{1-6}$-6alkyl or aryl, wherein
$PG^1$, $PG^2$, $PG^3$ and $PG^4$ are each independently protecting groups, wherein $PG^1$ is a protecting group that is removed by the first reducing agent and each $PG^2$ is the same or different or both $PG^2$ are joined to form a cyclic protecting group;

and wherein in the compounds of Formulae I(a)(i), VII(a), VIII(a), IX(a), X(a), XI(a)(i), XIII(a), XIV(a), XII(a), XVI(i), XVII, XVIII(i) and XV(i), one or more available hydrogens in A, $R^2$ and/or $R^3$ is/are optionally replaced with F and/or one or more of available atoms in A, $R^2$ and/or $R^3$ is/are optionally replaced with an isotopic label.

2. The process according to claim 1, wherein $PG^1$ is methyl.

3. The process according to claim 1, wherein both $PG^2$ are joined to form a cyclic protecting group.

4. The process according to claim 3, wherein both $PG^2$ are joined to form —$C(CH_3)_2$—.

5. The process according to claim 1, wherein the first reducing agent is $LiBH_4$.

6. The process according to claim 1, wherein the conditions to provide the compound of Formula VI comprise Swern oxidation conditions.

7. The process according to claim 1, wherein the source of singlet oxygen is provided by irradiating oxygen gas and tetraphenylporphyrin.

8. The process of claim 1, wherein the second reducing agent is thiourea.

9. The process of claim 1, wherein $PG^3$ is triisopropylsilane.

10. The process of claim 1, wherein the second oxidizing agent is 2-iodoxybenzoic acid.

11. The process according to claim 1, wherein the alkene-forming reagent of Formula XVII is a Wittig reagent.

12. The process according to claim 1, wherein the compound of Formula XV(i) is a compound of Formula XV(a)(i):

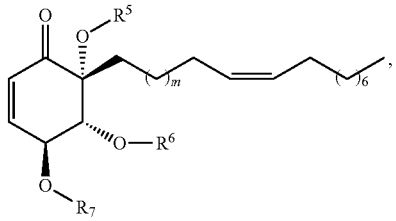

wherein m is 5, 7 or 9; and $R^5$, $R^6$ and $R^7$ are each independently H, $C_{1-6}$alkyl or aryl.

13. The process according to claim 1, wherein the compound of Formula XV(i) is a compound of Formula XV(b)(i):

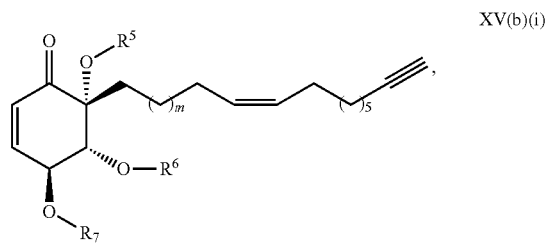

wherein m is 5, 7 or 9; and $R^5$, $R^6$ and $R^7$ are each independently H, $C_{1-6}$alkyl or aryl.

14. The process of claim 12, wherein m is 5.

15. The process of claim 12, wherein $R^5$, $R^6$ and $R^7$ are all H.

16. The process of claim 12, wherein the compound of Formula XV(a)(i) is a compound of the following structure:

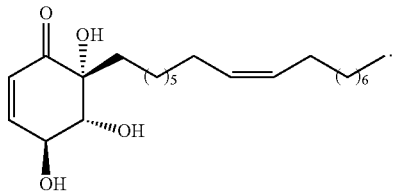

17. The process according to claim 1, wherein the conditions to convert $R^2$ into an aldehyde to provide the compound of Formula XVI(i) comprise selective hydrolysis of the acetal.

18. The process according to claim 17, wherein $R^2$ is —$C(OMe)_2$.

19. The process according to claim 1, wherein $PG^4$ is —S-phenyl.

20. The process according to claim 1, wherein the hydrogenation conditions to provide the compound of Formula XIV(a) comprise adding Wilkinson's catalyst to a solution of the compound of Formula XIII(a) in the presence of $H_2$.

* * * * *